United States Patent [19]

Parsons et al.

[11] Patent Number: 4,692,522
[45] Date of Patent: Sep. 8, 1987

[54] BENZOFUSED LACTAMS USEFUL AS CHOLECYSTOKININ ANTAGONISTS

[75] Inventors: William H. Parsons, Rahway; Arthur A. Patchett, Westfield, all of N.J.

[73] Assignee: Merck & Co., Inc., Rahway, N.J.

[21] Appl. No.: 871,340

[22] Filed: Jun. 6, 1986

Related U.S. Application Data

[63] Continuation-in-part of Ser. No. 718,597, Apr. 1, 1985, abandoned, which is a continuation-in-part of Ser. No. 624,856, Jun. 26, 1984, abandoned.

[51] Int. Cl.$^4$ .................. C07D 223/16; C07D 225/06; C07D 215/22
[52] U.S. Cl. ..................................... 540/523; 540/461; 546/158; 546/144; 546/148
[58] Field of Search ................ 540/523, 461; 546/158, 546/144, 148

[56] References Cited

U.S. PATENT DOCUMENTS

| 4,344,949 | 8/1982 | Hoefle | 424/258 |
| 4,385,051 | 5/1986 | Oka | 540/523 |
| 4,410,520 | 10/1983 | Watthey | 540/523 |
| 4,470,988 | 9/1984 | Watthey | 540/523 |
| 4,473,575 | 9/1984 | Watthey | 540/523 |
| 4,477,464 | 10/1984 | Slade | 540/412 |
| 4,537,885 | 8/1985 | Watthey | 540/523 |
| 4,575,503 | 3/1986 | Watthey | 540/523 |
| 4,600,534 | 7/1986 | Bach | 424/177 |

FOREIGN PATENT DOCUMENTS

| 84-283766 | 3/1984 | European Pat. Off. | 540/492 |
| 0166353 | 6/1985 | European Pat. Off. | 540/523 |
| 85-013488 | 12/1983 | Fed. Rep. of Germany | 492/ |
| 84-288219 | 4/1983 | World Int. Prop. O. | 540/492 |
| 85-062274 | 8/1983 | World Int. Prop. O. | 540/492 |

*Primary Examiner*—Robert T. Bond
*Attorney, Agent, or Firm*—Samuel B. Abrams; Hesna J. Pfeiffer

[57] ABSTRACT

Benzofused lactams and pharmaceutically-acceptable salts thereof which are useful as cholecystokinin antagonists.

3 Claims, No Drawings

BENZOFUSED LACTAMS USEFUL AS CHOLECYSTOKININ ANTAGONISTS

BACKGROUND OF THE INVENTION

The application is a continuation-in-part of application Ser. No. 718,597, filed Apr. 1, 1985, now abandoned, which is a continuation-in-part of application Ser. No. 624,856, filed June 26, 1984, now abandoned.

Cholecystokinins (CCK) are neuropeptides which include CCK-33, a neuropeptide of thirty-three amino acids in its originally-isolated form (see, Mutt and Jorpes, *Biochem. J.* 125 678 (1971)), its carboxyl terminal octapeptide, CCK-8 (a naturally-occurring neuropeptide also, and the minimum fully-active sequence), and 39- and 12-amino acid forms. CCK's are believed to be physiological satiety hormones and, therefore, may play an important role in appetite regulation (G. P. Smith, *Eating and Its Disorders*, A. J. Stunkard and E. Stellar, Eds., Raven Press, New York, 1984, p. 67). They exist in both gastrointestinal tissue and in the central nervous system (V. Mutt, *Gastrointestinal Hormones*, G. B. J. Glass, Ed., Raven Press, N.Y., (1980) p. 169).

Among additional effects, CCK's stimulate colonic motility, gall bladder contraction and pancreatic enzyme secretion, and they inhibit gastric emptying. CCK's reportedly co-exist with dopamine in certain mid-brain neurons and thus may also play a role in the functioning of dopaminergic systems in the brain, as well as serving as neurotransmitters in their own right. See: A. J. Prange et al., "Peptides in the Central Nervous System", *Ann. Repts. Med. Chem.* 17 31, 33 (1982) and references cited therein; J. A. Williams, *Biomed. Res.* 3, 479 107 (1982); and J. E. Morley, *Life Sci.* 30 (1982).

Antagonists of CCK's have been useful for preventing and treating CCK-related disorders of the gastrointestinal, central nervous and appetite regulatory systems of animals, especially of humans. CCK antagonists are also useful in potentiating and prolonging opiate-mediated analgesia, and thus have utility in the treatment of pain [see, P. L. Faris et al., *Science* 226, 1215 (1984)].

Three distinct chemical classes of CCK-receptor antagonists have been reported. The first class comprises derivatives of cyclic nucleotide, of which dibutyryl cyclic GMP has been shown to be the most potent be detailed structure-function studies (see: N. Barlos et al., *Am. J. Physiol.*, 242, G161 (1982) and P. Robberecht et al., *Mol., Pharmacol.,* 17, 268 (1980)). The second class comprises peptide antagonists which are C-terminal fragments and analogs of CCK, of which both shorter (Boc-Met-Asp-Phe-NH$_2$, Met-Asp-Phe-NH$_2$) and longer (Cbz-Tyr(SO$_3$H)-Met-Gly-Trp-Met-Asp-NH$_2$) C-terminal fragments of CCK's can function as CCK antagonists, according to recent structure-function studies [see: R. T. Jensen et al., *Biochim. Boiphys. Acta.,* 757, 250 (1983) and M. Spanarkel et al., *J. Biol. Chem.,* 258, 6746 (1983)]. The latter compound was recently reported to be a partial agonist [see, J. M. Howard et al., *Gastroenterology* 86 (5) Part 2, 1118 (1984)]. Then, the third class of CCK receptor antagonists comprises the amino acid derivatives, proglumide, a derivative of glutaramic acid, and the N-acyl tryptophans, including para-chlorobenzoyl-L-tryptophan (benzotript) [see, W.F. Hahne et al., *Proc. Natl. Acad. Sci. U.S.A.,* 78, 6304 (1981) and R. T. Jensen et al., *Biochem. Biophys. Acta.,* 761, 269 (1983)]. All of these compounds, however, are relatively weak antagonists of CCK (IC$_{50}$:generally 10$^4$M, but down to 10$^{-6}$M in the case of peptides), and the peptide CCK-antagonists have substantial stability and absorption problems.

It was, therefore, an object of this invention to identify substances which more effectively antagonize the function of cholecystokinins in disease states in mammals, especially in humans. It was another object of this invention to develop a method of antagonizing the functions of cholecystokinins in disease states in mammals. It was still another object of this invention to develop a method of preventing or treating disorders of the gastrointestinal, central nervous and appetite regulatory systems of mammals, especially of humans.

SUMMARY OF THE INVENTION

It has now been found that the benzofused lactams of this invention are antagonists of cholecystokinins (CCK), which are useful in the treatment and prevention of CCK-related disorders of the gastrointestinal, central nervous and appetite regulatory systems of mammals, especially of humans.

DETAILED DESCRIPTION OF THE INVENTION

The compounds of this invention are benzofused lactams of the formula:

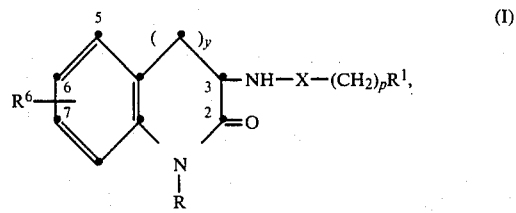

wherein:
X is absent or carbonyl;
R is
unsubstituted or mono-, di-, or trisubstituted C$_1$–C$_8$-straight- or branched-alkyl, where the substituent(s) is/are selected from the group consisting of C$_1$–C$_4$-alkylthio, C$_1$–C$_4$-alkyloxy, C$_1$–C$_4$-alkylamino, unsubstituted or mono-, di-, or trisubstituted C$_6$- or C$_{10}$-aryloxy, unsubstituted or mono-, di-, or trisubstituted C$_6$- or C$_{10}$-arylthio, unsubstituted or mono-, di-, or trisubstituted C$_6$- or C$_{10}$-aryl, and unsubstituted or mono-, di-, or trisubstituted hetero-C$_3$–C$_9$-aryl, the one-to-three heteroatoms in the hetero-C$_3$–C$_9$-aryl being selected from O, S and N atoms, and the substituent(s) on the C$_6$- or C$_{10}$-aryloxy, the C$_6$- or C$_{10}$-arylthio, the C$_6$- or C$_{10}$-aryl and the hetero-C$_3$–C$_9$-aryl being selected from C$_1$–C$_8$-straight- or branched-alkyl, hydroxy, C$_1$–C$_4$-alkoxy, halo, nitro, amino, C$_1$–C$_4$-alkylthio or mono- or di-C$_1$–C$_4$-alkylamino;
substituted carbonyl-C$_1$–C$_4$-alkyl, which carbonyl group is substituted with hydroxy, C$_1$–C$_8$-straight- or branched-alkoxy, C$_1$–C$_8$-straight- or branched-alkyl, unsubstituted or mono-, di-, or trisubstituted C$_6$- or C$_{10}$-aryl, unsubstituted or mono-, di- or trisubstituted C$_6$- or C$_{10}$-aryl-C$_1$–C$_8$-alkyl, and unsubstituted or mono-, di-, or trisubstituted C$_6$- or C$_{10}$-aryl-C$_1$–C$_4$-alkoxy, where the substituent(s) on the $C_6$- or $C_{10}$-aryl, the $C_6$- or $C_{10}$-aryl-$C_1$-$C_8$-alkyl or the $C_6$- or $C_{10}$-aryl-$C_1$-$C_4$-alkoxy is/are selected from the groups consisting of hydroxy, $C_1$-$C_8$-straight- or branched-alkyl, $C_1$-$C_4$-alkoxy, halo, nitro, amino, $C_1$-$C_4$-alkylthio, and mono- or di-$C_1$-$C_4$-alkylamino, or $NR^4R^5$, where $R^4$ and $R^5$ are independently selected from hydrogen, $C_1$-$C_6$-straight- or branched-alkyl, unsubstituted or mono-, di-, or trisubstituted-carboxy-$C_1$-$C_8$-straight- or branched-alkyl, or unsubstituted or mono-, di-, or trisubstituted-carboxamido-$C_1$-$C_8$-straight- or branched-alkyl, wherein the substituent(s) on the carboxy-$C_1$-$C_8$-straight- or branched-alkyl or on the carboxamido-$C_1$-$C_8$-straight- or branched-alkyl is/are selected from the group consisting of $C_1$-$C_4$-alkyl, $C_1$-$C_4$-alkoxy, amino-$C_1$-$C_4$-alkyl, unsubstituted or mono-, di-, or trisubstituted $C_6$- or $C_{10}$-aryl, unsubstituted or mono-, di- or trisubstituted $C_6$- or $C_{10}$-aryl-$C_1$-$C_8$-alkyl, and unsubstituted or mono-, di-, or trisubstituted $C_6$- or $C_{10}$-aryl-$1C_{10}$-aryl-$C_1$-$C_4$-alkoxy, where the substituent(s) on the $C_6$- or $C_{10}$-aryl, the $C_6$- or $C_{10}$-aryl-$C_1$-$C_8$-alkyl or the $C_6$- or $C_{10}$-aryl-$C_1$-$C_4$-alkoxy is/are selected from the group consisting of hydroxy, $C_1$-$C_8$-straight- or branched-alkyl, $C_1$-$C_4$-alkoxy, halo, nitro, amino, $C_1$-$C_4$-alkylthio, and mono- or di-$C_1$-$C_4$-alkylamino;

$R^1$ is $R^a$ or $R^b$;

$R^a$ is unsubstituted or mono-, di- or trisubstituted aryl, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino;

unsubstituted or mono-, di- or trisubstituted hetero-$C_3$-$C_9$-aryl, the one-to-three heteroatoms of which are selected from O, N and S atoms and the substitutent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino;

unsubstituted or mono-, di- or trisubstituted $C_6$- or $C_{10}$-aryl-$C_1$-$C_8$-straight- or branched-alkyl, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino;

unsubstituted or mono-, di- or trisubstituted hetero-$C_3$-$C_9$-aryl-$C_1$-$C_8$-straight- or branched-alkyl, the one-to-three heteroatoms of which are selected from O, N and S and the substituent(s) is/are selected from the group consisting of $C_1$-$C_8$-straight- or branched alkyl, hydroxy, $C_1$-$C_4$-alkoxy, halo, nitro, amino, $C_1$-$C_4$-alkylthio and mono- or di-$C_1$-$C_4$-alkylamino;

unsubstituted or mono-, di- or trisubstituted $C_6$- or $C_{10}$-aryl-$C_2$-$C_4$-alkenyl, where the substituent(s) is/are selected from the group consisting of $C_1$-$C_8$-straight- or branched- alkyl, hydroxy, $C_1$-$C_4$-alkoxy, halo, nitro, amino, $C_1$-$C_4$-alkylthio and mono- or di- $C_1$-$C_4$ alkylamino;

unsubstituted or mono-, di- or trisubstituted hetero-$C_3$-$C_9$-aryl-$C_2$-$C_4$-alkenyl, the one-to-three heteroatoms of which are selected from O, N and S atoms, and the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino;

unsubstituted or mono-, di- or trisubstituted $C_6$- or $C_{10}$-aryloxy, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkyl-thio and mono- or di-$C_1$-$C_4$-alkylamino;

unsubstituted or mono-, di- or trisubstituted hetero-$C_3$-$C_9$-aryloxy, the one-to-three hetero-atoms of which are selected from O, N and S atoms, and the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino;

unsubstituted or mono-, di- or trisubstituted $C_6$- or $C_{10}$-arylthio, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio or mono- or di-$C_1$-$C_4$-alkylamino;

unsubstituted or mono-, di- or trisubstituted hetero-$C_3$-$C_9$-arylthio, the one-to-three hetero-atoms of which are selected from O, N and S atoms, and the substituent(s) is/are selected from the group consisting of $C_1$-$C_8$-straight- or branched alkyl, hydroxy, $C_1$-$C_4$-alkoxy, halo, nitro, amino, $C_1$-$C_4$-alkylthio or mono- or di-$C_1$-$C_4$-alkylamino;

unsubstituted or mono-, di- or trisubstituted $C_6$- or $C_{10}$-aryl-$C_1$-$C_4$-alkyloxy, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio or mono- or di-$C_1$-$C_4$-alkylamino;

unsubstituted or mono-, di- or trisubstituted hetero-$C_3$-$C_9$-aryl-$C_1$-$C_4$-alkyloxy, the one-to-three heteroatoms of which are selected from O, N and S atoms, and the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio or mono- or di-$C_1$-$C_4$-alkylamino;

unsubstituted or mono-, di- or trisubstituted $C_6$- or $C_{10}$-aryl-$C_1$-$C_4$-alkylthio, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-di-$C_1$-$C_4$-alkylamino;

unsubstituted or mono-, di- or trisubstituted hetero-$C_3$-$C_9$-aryl-$C_1$-$C_4$-alkylthio, the one-to-three heteroatoms of which are selected from O, N and S atoms, and the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino;

$C_1$-$C_8$-straight- or branched-alkyls;

$C_3$-$C_{10}$-cycloalkyl;

$C_3$-$C_{10}$-cycloalkyl-$C_1$-$C_4$-alkyl;

$C_1$-$C_6$-straight- or branched-alkyl-Q-$(CH_2)_m$, where m is 1-to-3, and Q is O, S, SO, $SO_2$, —HC=CH—, or substituted-amino, wherein the substituent is hydrogen, $C_1$–$C_8$-straight- or branched-alkyl, unsubstituted or mono-, di- or trisubstituted $C_6$- or $C_{10}$-aryl, unsubstituted or mono-, di- or trisubstituted hetero-$C_3$–$C_9$-aryl, the one-to-three heteroatoms of which are selected from O, N and S atoms, unsubstituted or mono-, di- or trisubstituted $C_6$- or $C_{10}$-aryl-$C_1$–$C_4$-alkyl, or unsubstituted or mono-, di- or trisubstituted hetero-$C_3$–$C_9$-aryl-$C_1$–$C_4$-alkyl, the one-to-three heteroatoms of which are selected from O, N and S, where the substituent(s) on the $C_6$- or $C_{10}$-aryl, the hetero-$C_3$–$C_9$-aryl, the $C_6$- or $C_{10}$-aryl-$C_1$–$C_4$-alkyl, or the hetero-$C_3$–$C_9$-aryl-$C_1$–$C_4$-alkyl is/are selected from the group consisting of $C_1$–$C_8$-straight- or branched-alkyl, hydroxy, $C_1$–$C_4$-alkoxy, halo, nitro, amino, $C_1$–$C_4$-alkyl-thio and mono- or di-$C_1$–$C_4$-alkylamino;

$C_9$–$C_{12}$-benzofused cycloalkyls; or $C_8$–$C_{10}$-benzofused heterocycloalkyls, the one heteroatom of which is selected from O, N and S; and $R^b$ is —$CHR^2R^3$, where $R^2$ is $R^a$, as defined above, and $R^3$ is substituted carbonyl, wherein the substituent is hydroxy, $C_1$–$C_4$-alkoxy, $C_1$–$C_4$-alkyl, hydroxy-$C_1$–$C_4$-alkyl, amino, $C_1$–$C_8$-straight- or branched-alkylamino, $C_6$- or $C_{10}$-aryloxy, $C_6$- or $C_{10}$-aryl-$C_1$–$C_6$-alkylamino, $C_6$- or $C_{10}$-aryl-$C_1$–$C_4$-alkyloxy, carboxy-$C_1$–$C_8$-straight- or branched-alkylamino, or carboxamido-$C_1$–$C_8$-straight- or branched-alkylamino;

$NR^7R^8$, wherein $R^7$ and $R^8$ are independently selected from hydrogen, substituted carbonyl, unsubstituted or mono-, di- or trisubstituted-carboxy-$C_1$–$C_8$-straight- or branched-alkyl, and unsubstituted- or mono-, di- or trisubstituted-carboxamido-$C_1$–$C_8$-straight- or branched-alkyl, where the substituents on the carbonyl, the carboxy-$C_1$–$C_8$-alkyl or the carboxamido-$C_1$–$C_8$-alkyl is/are selected from $C_1$–$C_4$-alkyl, $C_1$–$C_4$-alkyloxy, amino- $C_1$–$C_4$-alkyl, unsubstituted or mono-, di- or trisubstituted $C_6$- or $C_{10}$-aryl-$C_1$–$C_8$-alkyl, unsubstituted- or mono-, di- or trisubstituted $C_6$- or $C_{10}$-aryl, unsubstituted- or mono-, di- or trisubstituted $C_6$- or $C_{10}$-aryl-$C_1$–$C_4$-alkoxy, and mono-, di- or trisubstituted-$C_1$–$C_8$-alkyl, wherein the substituents(s) on the $C_6$- or $C_{10}$-aryl-$C_1$–$C_8$-alkyl, the $C_6$- or $C_{10}$-aryl, the $C_6$- or $C_{10}$-aryl-$C_1$–$C_4$-alkoxy or the $C_1$–$C_8$-alkyl is/are selected from hydroxy, $C_1$–$C_8$-straight- or branched-alkyl, $C_1$–$C_4$-alkoxy, halo, nitro, amino, $C_1$–$C_4$-alkylthio, or mono- or di-$C_1$–$C_4$-alkylamino;

$R^6$ is hydrogen;
halo;
hydroxy;
nitro;
amino;
$C_1$–$C_4$-alkylamino;
$C_1$–$C_8$-alkyl; or
$C_1$–$C_8$-alkoxy;

y is 1 to 3;

p is 0 to 2, with the proviso that when p is O, X is carbonyl;

and the pharmaceutically-acceptable salts thereof.

The compounds according to the present invention may be racemic mixtures or R or S enantiomer forms of these compounds.

The straight-chain, brached saturated and unsaturated hydrocarbons (alkyl and alkenyl) recited above are represented by such compounds as methyl, ethyl, n-propyl, i-propyl, n-butyl, i-butyl, t-butyl, n-pentyl, i-pentyl, n-hexyl; and vinyl, allyl, butenyl, and the like. The cycloalkyl and cyclo-$C_1$–$C_4$-alkyl substituents are represented, respectively, by groups such as cyclopropyl, cyclobutyl and cyclohexyl through cyclodecyl and by groups such as cyclopentylethyl, cyclohexylpropyl and cycloheptylmethyl.

The alkoxy substituent represents an alkyl group attached through an oxygen bridge.

The arylalkyl and heteroarylalkyl groups recited above represent aryl or heteroaryl groups as herein defined attached through a straight- or branched-chain alkyl group of from one to eight carbon atoms, such as, for example, benzyl, phenethyl, 3,3-diphenylpropyl, 3-indolylmethyl, and the like.

Halo means chloro, bromo, iodo, or fluoro.

The aryl substituent is illustrated by phenyl, naphthyl, or biphenyl.

The heteroaryl substituent recited above represents any 5- or 6-membered aromatic ring containing from one-to-three O, N or S heteroatoms such as, for example, pyridyl, thienyl, furyl, imidazolyl, and thiazolyl, as well as any bicyclic group in which any of the above heterocyclic rings is fused to a benzene ring such as, for example, indolyl, quinolinyl, isoquinolinyl, benzimidazolyl, benzothiazolyl, and benzthienyl.

The Formula I compounds which bear acidic or basic groups may be used in the form of salts derived from inorganic or organic acids and bases, whereby water- or oil-soluble or dispersible products are obtained. Included among such acid addition salts are acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts, such as sodium and potassium salts, alkaline earth metal salts, such as calcium and magnesium salts, salts with organic bases such as dicyclohexylamine and N-methyl-D-glucamine, and salts with amino acids such as arginine, lysine, and so forth.

In the compounds of Formula I, the preferred stereochemistry at the 3-position is R, the preferred ring size is realized when y is 2 or 3, and the preferred side chain off the the lactam is one wherein X is carbonyl, most preferably when p is 0.

Preferred compounds according to the present invention include:

1-carbomethoxymethyl-3-(3-indolemethyl-)aminohomodihydrocarbostyril;

1-carboxymethyl-3-(carbonyl-2-indolyl-)aminohomodihydrocarbostyril;

1-t-butoxycarbonylmethyl-3-(2-naphthylacetyl-)aminohomodihydrocarbostyril;

1-t-butoxycarbonylmethyl-3-(D-N-acetyltryptophanyl-)aminohomodihydrocarbostyril;

1-t-butoxycarbonylmethyl-3-(L-N-acetyltryptophanyl-)aminohomodihydrocarbostyril;

1-t-butoxycarbonylmethyl-3-(L-N-carbobenzyloxytryptophanyl)aminohomodihydrocarbostyril;

1-t-butoxycarbonylmethyl-3-(D-N-carbobenzyloxytryptophanyl)aminohomodihydrocarbostyril;

1-t-butoxycarbonylmethyl-3-(carbonyl-2-indolyl-)aminohexahydrobenzoazocine-2-one;

1-t-butoxycarbonylmethyl-3-(2-naphthoyl-)aminohomodihydrocarbostyril;

1-t-butoxycarbonylmethyl-3-(2-naphthylmethyl-)aminohomodihydrocarbostyril;

1-t-butoxycarbonylmethyl-3-(carbonyl-2-indolyl-)aminohomodihydrocarbostyril;

1-t-butoxycarbonylmethyl-3-(2-naphthylmethyl-)aminohomodihydrocarbostyril;

1-t-butoxycarbonylmethyl-3-(3,4-dichlorobenzoyl-)aminohomodihydrocarbostyril;

1-t-butoxycarbonylmethyl-3-(2-indolemethyl-)aminohomodihydrocarbostyril;

1-t-butoxycarbonylmethyl-3-(3,4-dichlorobenzyl-)aminohomodihydrocarbostyril;

1-benzyl-3-(carbonyl-2-indolyl)aminohomodihydrocarbostyril;

1-ethoxycarbonylmethyl-3-(2-naphthoyl-)aminohomodihydrocarbostyril;

1-t-butoxycarbonylmethyl-3(R)-(2-indolemethyl-)aminohomodihydrocarbostyril;

1-t-butoxycarbonylmethyl-3(R)-(3,4-dichlorobenzyl-)aminohomodihydrocarbostyril;

1-t-butoxycarbonylmethyl-3(R)-(2-naphthylmethyl)-aminohomodihydrocarbostyril;

1-t-butoxycarbonylmethyl-3(R)-(2-naphthoyl-)aminohomodihydrocarbostyril; and 1-t-butoxycarbonylmethyl-3(R)-(carbonyl-2-indolyl-)aminohomodihydrocarbostyril.

More preferred compounds according to this invention include:

1-carboxymethyl-3-(carbonyl-2-indolyl-)aminohomodihydrocarbostyril;

1-benzyl-3-(carbonyl-2-indolyl)aminohomodihydrocarbostyril;

1-t-butoxycarbonylmethyl-3-(carbonyl-2-indolyl-)aminohomodihydrocarbostyril;

1-t-butoxycarbonylmethyl-3-(2-indolemethyl-)aminohomodihydrocarbostyril;

1-t-butoxycarbonylmethyl-3-(3,4-dichlorobenzyl-)aminohomodihydrocarbostyril;

1-t-butoxycarbonylmethyl-3(R)-(2-indolemethyl-)aminohomodihydrocarbostyril;

1-t-butoxycarbonylmethyl-3(R)-(3,4-dichlorobenzyl-)aminohomodihydrocarbostyril;

1-t-butoxycarbonylmethyl-3(R)-(2-naphthylmethyl-)aminohomodihydrocarbostyril;

1-t-butoxycarbonylmethyl-3(R)-(2-naphthoyl-)aminohomodihydrocarbostyril; and 1-t-butoxycarbonylmethyl-3(R)-(carbonyl-2-indolyl-)aminohomodihydrocarbostyril.

The ability of the compounds of Formula I to antagonize CCK makes these compounds especially useful in the treatment and prevention of disease states in mammals, especially in humans, wherein CCK may be involved. These disease states include, for example, gastrointestinal disorders, such as irritable bowel syndrome, ulcers, excess pancreatic or gastric secretion, acute pancreatis, motility disorders, central nervous system disorders caused by CCK's interaction with dopamine, such as neuroleptic disorders, tardive, dyskinesia, Parkinson's disease, psychosis or Gilles de la Tourette Syndrome, and disorders of appetite regulatory systems or pain.

Screening of the novel benzofused lactams according to the present invention to determine biological activity and obtain an $IC_{50}$ value for them, in order to identify significant CCK-antagonism, has been accomplished using an $^{125}$I-CCK-receptor binding assay and in vitro isolated tissue preparations.

CCK receptor binding (pancreas) method

CCK-33 was radiolabeled with $^{125}$I-Bolton Hunter reagent (2000 Ci/mmole) as described by Sankara et al. [J. Biol. Chem. 254: 9349–9351, (1979)]. Receptor binding was performed according to Innis and Snyder [Pro. Natl. Acad. Sci. 77: 6917–6921, (1980)], with the minor modification of adding the additional protease inhibitors, phenylmethane sulfonyl fluoride and o-phenanthroline, which have no effect on the $^{125}$I-CCK receptor binding assay.

The whole pancreas of a male Sprague-Dawley rat (200–350 g), which had been sacrificed by decapitation, was dissected free of fat tissue and homogenized in 20 volumes of ice-cold 50 mM, Tris HCl (pH 7.7 at 25° C.) with a Brinkman Polytron PT 10. The homogenates were centrifuged at 48,000 g for 10 minutes, then the resulting pellets were resuspended in Tris Buffer, centrifuged as above, and resuspended in 200 volumes of binding assay buffer (50 mM Tris HCl, pH 7.7 at 25° C., 5 mM dithiothriethel, 0.1 mM bacitracin, 1.2 mM phenylmethane sulfonyl fluoride and 0.5 mM o-phenanthroline).

For the binding assay, 25 μl of buffer (for total binding), or unlabeled CCK-8 sulfate sufficient to give a final concentration of 1 μM (for nonspecific binding) or the compounds of Formula I according to the instant invention (for determination of inhibition of antagonism to $^{125}$I-CCK-binding) and 25 μl of $^{125}$I-CCK-33 (30,000–40,000 cpm) were added to 450 μl of the membrane suspensions in microfuge tubes. All assays were run in duplicate or triplicate, and the reaction mixtures were incubated at 37° C. for 30 minutes and centrifuged in a Beckman Microfuge (4 minutes) immediately after adding 1 ml of ice-cold incubation buffer. The supernatant was aspirated and discarded, and the pellets were counted with a Beckman Gamma 5000. For Scatchard analysis to determine the mechanism of inhibition of $^{125}$I-CCK-33 binding by the most potent compounds (Ann. N.Y. Acad. Sci., 51, 660, 1949), $^{125}$I-CCK-33 was progressively diluted with increasing concentrations of CCK-33.

CCK receptor binding (Brain) method

CCK-33 was radiolabeled and the binding was performed according to the description for the pancreas method with modifications according to Saito, et al. (J. Neurochem, 37, 483–490 (1981)).

Male Hartley guinea pigs (300–500 g) were sacrificed by decapitation, and the brains were removed and placed in ice-cold 50 mM, Tris HCl plus 7.58 g/l Trizma-7.4 (pH 7.4 at 25° C.). The cerebral cortex was dissected and used as a receptor source, and each gram of fresh guinea pig brain tissue was homogenized in 10 ml of Tris/Trizma buffer with a Brinkman Polytron PT-10. The homogenates were centrifuged at 42,000 g for 15 minutes, then the resulting pellets were resuspended in Tris Buffer, centrifuged as above and resuspended in 200 volumes of binding assay buffer (10 mM of N-2- hydroxy-ethylpiperazine-N'-2-ethane-sulfonic acid (HEPES), pH 7.7 at 25° C., 5 mM MgCl$_2$, 1 mM ethylene glycol-bis-$\beta$-amino-ethyl-ether-N,N'-tetraacetic acid (EGTA), 0.4% BSA (bovine serum albumin) and 0.25 mg/ml bacitracin, pH 6.5).

The remainder of the binding assay was as described for the pancreas method, except that the reaction mixtures were incubated at 25° C. for 2 hours before centrifugation.

In Vitro Effect of Representative Compounds of Formula I on $^{125}$I-CCK-33 Receptor Binding Compounds of Formula I competitively inhibited specific $^{125}$I-CCK-33 binding in a concentration-dependent manner with an IC$_{50}$ (pancreas) of less than or equal to 100 $\mu$M, such as, for example:

1-t-butoxycarbonylmethyl-3-(D-N-acetyltryptophanyl-)aminohomodihydrocarbostyril, IC$_{50}$=1.6 $\mu$M;
1-t-butoxycarbonylmethyl-3-(L-N-acetyltryptophanyl-)aminohomodihydrocarbostyril, IC$_{50}$=2.8 $\mu$M;
1-t-butoxycarbonylmethyl-3-(L-N-carbobenzyloxytryptophanyl)aminohomodihydrocarbostyril, IC$_{50}$=1.2 $\mu$M;
1-methyl-3-(1-carboethoxy-3-phenyl-1-propyl-)aminohomodihydrocarbostyril, IC$_{50}$=60 $\mu$M;
1-carbomethoxymethyl-3-(3-indolemethyl-)aminohomodihydrocarbostyril, IC$_{50}$=15 $\mu$M;
1-benzyl-3-(carbonyl-2-indolyl)aminohomodihydrocarbostyril, IC$_{50}$=65 nM;
1-ethoxycarbonylmethyl-3-(2-naphthoyl-)aminohomodihydrocarbostyril, IC$_{50}$=110 nM;
1-methyl-3-(2-naphthoyl)aminohomodihydrocarbostyril, IC$_{50}$=8700 nM;
1-t-butoxycarbonylmethyl-3-(2-naphthylacetyl-)aminohomodihydrocarbostyril, IC$_{50}$=3000 nM;
1-t-butoxycarbonylmethyl-3-(carbonyl-2-indolyl-)aminohomodihydrocarbostyril, IC$_{50}$=20 nM;
1-t-butoxycarbonylmethyl-3-(carbonyl-2-indolyl-)aminohexahydrobenzoazocine-2-one, IC$_{50}$=80 nM;
1-t-butoxycarbonylmethyl-3-(carbonyl-2-indolyl-)aminodihydrocarbostyril, IC$_{50}$=130 nM;
1-t-butoxycarbonylmethyl-3(S)-(carbonyl-2-indolyl-)aminohomodihydrocarbostyril, IC$_{50}$=640 nM;
1-t-butoxycarbonylmethyl-3(R)-(carbonyl-2-indolyl-)aminohomodihydrocarbostyril, IC$_{50}$=8.7 nM;
1-t-butoxycarbonylmethyl-3-(2-naphthoyl-)aminohomodihydrocarbostyril, IC$_{50}$=9.4 nM;
1-t-butoxycarbonylmethyl-3(R)-(2-naphthoyl-)aminohomodihydrocarbostyril, IC$_{50}$=4.7 nM;
1-t-butoxycarbonylmethyl-3(R)-(2-naphthylmethyl-)aminohomodihydrocarbostyril, IC$_{50}$=4 nM;
1-t-butoxycarbonylmethyl-3-(2-naphthylmethyl-)aminohomodihydrocarbostyril, IC$_{50}$=8.7 nM;
1-t-butoxycarbonylmethyl-3-(benzoyl)aminohomodihydrocarbostyril, IC$_{50}$=4600 nM;
1-t-butoxycarbonylmethyl-3-(4-chlorobenzoyl-)aminohomodihydrocarbostyril, IC$_{50}$=500 nM; and
1-t-butoxycarbonylmethyl-3-(3,4-dichlorobenzoyl-)aminohomodihydrocarbostyril, IC$_{50}$=100 nM.

Thus, in accordance with the present invention, there is provided a pharmaceutical composition for and a method of treating gastrointestinal disorders, central nervous system disorders, or regulating appetite, which comprises administering to a patient in need of such treatment a pharmaceutically-effective amount of a compound of Formula I.

For administration, the compositions of the invention may also contain other conventional pharmaceutically-acceptable compounding ingredients, as necessary or desired, such as carriers or diluents. Conventional procedures for preparing such compositions in appropriate dosage forms may be utilized, in order to assure that in whatever dosage form, the composition will contain a pharmaceutically-effective amount of the compounds of the invention.

The present compositions may be administered orally or other-than-orally (e.g., parenterally, by insufflation, topically, rectally, etc.), using appropriate dosage forms (e.g., tablets, capsules, suspensions, solutions, and the like, for oral administration; suspension emulsions, and the like, for parenteral administration; solutions for intravenous administration; and ointments, transdermal patches, and the like, for topical administration).

Compositions intended for oral use may be prepared according to any method known to the art for the manufacture of pharmaceutical compositions, and such tablets or other compositions may contain one or more agents selected from the group consisting of sweetening agents, flavoring agents, coloring agents, preserving agents, and non-toxic excipients in order to provide pharmaceutically-elegant and palatable preparations. The excipients used may be, for example (1) inert diluents, such as calcium carbonate, sodium carbonate, lactose, calcium phosphate or sodium phosphate; (2) granulating and disintegrating agents, such as corn starch, or alginic acid; (3) binding agents, such as starch, gelatin or acacia, and (4) lubricating agents, such as magnesium stearate, stearic acid or talc. The tablets may be uncoated or they may be coated by known techniques with, for example, glyceryl monostearate or glyceryl distearate as a time delay material, to delay disintegration and absorption in the gastrointestinal tract and thereby provide a sustained action over a longer period. They may also be coated by the techtechniques described in U.S. Pat. Nos. 4,256,108; 4,160,452; and 4,265,874 to form osmotic therapeutic tablets for controlled release. In some cases, these formulations for oral use may be in the form of hard gelatin capsules, wherein the active ingredient is mixed with an inert solid diluent, such as calcium carbonate, calcium phosphate or kaolin, or in the form of soft gelatin capsules wherein the active ingredient is mixed with water or an oil medium, such as peanut oil, liquid paraffin, or olive oil.

Aqueous suspensions normally contain the active materials in admixture with excipients suitable for the manufacture of aqueous suspensions. Such excipients include: (1) suspending agents, such as sodium carboxymethylcellulose, methylcellulose, hydroxypropylmethylcellulose, sodium alginate, polyvinylpyrrolidone, gum tragacanth and gum acacia; (2) dispersing or wetting agents which may be (a) a naturally-occurring phosphatide, such as lecithin; (b) a condensation product of an alkylene oxide with a fatty acid, for example, polyoxyethyolene stearate; (c) a condensation product of ethylene oxide with a long chain aliphatic alcohol, for example, heptadecaethyleneoxycetanol; (d) a condensation product of ethylene oxide with a partial ester derived from a fatty acid and a hexitol, such as polyoxyethylene sorbitol monooleate; or (e) a condensation product of ethylene oxide with a partial ester derived from a fatty acid and a hexitol anhydride, for example, polyoxyethylene sorbitan monooleate.

The aqueous suspensions may also contain one or more preservatives, such as ethyl or n-propyl p-hydroxybenzoate; one or more coloring agents; one or more flavoring agents; and one or more sweetening agents, such as sucrose or saccharin. Oily suspensions may be formulated by suspending the active ingredient in a vegetable oil, such as arachis oil, olive oil, sesame oil or coconut oil, or in a mineral oil such as liquid paraffin, and may contain a thickening agent, such as beeswax, hard paraffin or cetyl alcohol. Sweetening agents and flavoring agents may be added to provide a palatable oral preparation, and these compositions may be preserved by the addition of an antioxidant, such as ascorbic acid.

Dispersible powders and granules, which provide the active ingredient in admixture with a dispersing or wetting agent, a suspending agent and one or more preservatives, are suitable for the preparation of an aqueous suspension. Suitable dispersing or wetting agents, suspending agents, and sweetening, flavoring and coloring agents described above may also be present.

The pharmaceutical compositions of the invention may be in the form of oil-in-water emulsions. The oily phase may be a vegetable oil, such as olive oil or arachis oils, or a mineral oil, such as liquid paraffin or a mixture thereof. Suitable emulsifying agents include (1) naturally-occurring gums, such as gum acacia and gum tragacanth, (2) naturally-occurring phosphatides, such as soy bean and lecithin, (3) esters or partial esters derived from fatty acids and hexitol anhydrides, such as sorbitan monooleate, and (4) condensation products of said partial esters with ethylene oxide, for example, polyoxyethylene sorbitan monooleate. These emulsions may also contain sweetening and flavoring agents.

Syrups and elixirs may be formulated with sweetening agents, for example, glycerol, propylene glycol, sorbitol or sucrose, and may also contain a demulcent, a preservative and flavoring and coloring agents.

These compositions may be in the form of a sterile injectable aqueous or oleagenous suspension, formulated according to known methods using those suitable dispersing or wetting agents and suspending agents mentioned above. The injectable preparation may also be a sterile injectable solution or suspension in a non-toxic parenterally-acceptable diluent or solvent, for example, as a solution in 1,3-butane diol, Among the acceptable vehicles, suspending medium and solvents that may be employed are water, Ringer's solution, isotonic sodium chloride solution, and sterile, fixed oils.

For this purpose, any bland fixed oil may be employed, including synthetic mono- or diglycerides, and fatty acids, such as oleic acid.

A composition of the invention may also be administered in the form of suppositories for rectal administration of the drug. These compositions may be prepared by mixing the drug with a suitable non-irritating excipient, such as cocoa butter or polyethylene glycols, which is solid at ordinary temperatures, but liquid at the rectal temperature and will therefore melt in the rectum to release the drug.

For topical use, creams, ointments, jellies, solutions or suspensions, and other forms, containing the compositions of the invention, are employed.

Treatment dosage for human beings may be varied, as determined by the administering professional, but daily dosages of the compounds of the invention generally range from about 0.5 mg to about 1,000 mg, and preferably, from about 5 mg to about 500 mg. The amount of active ingredient that may be combined with the carrier materials to produce a single dosage form will vary depending upon the host treated and the particular mode of administration. For example, a formulation intended for oral administration may contain, for example, from 5 mg to 500 mg of active agent compounded with an appropriate and convenient amount of carrier material which may vary from about 5 to about 95 percent of the total composition.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of Formula I may be prepared by the methods shown in the following Reaction Scheme, wherein R, $R^1$, $R^2$, $R^3$, $R^4$, $R^5$ and $R^6$, y and p are as defined above, unless otherwise indicated. Also, as will be evident to those skilled in the art and as demonstrated in the Examples hereinafter, reactive groups not involved in the reactions, such as amino, carboxy, mercapto, etc., may be protected by methods standard in peptide chemistry prior to the coupling reactions and subsequently deprotected to obtain the desired products.

REACTION SCHEME

Process A

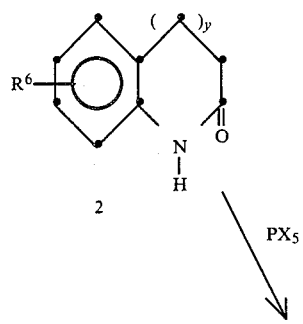

-continued
REACTION SCHEME
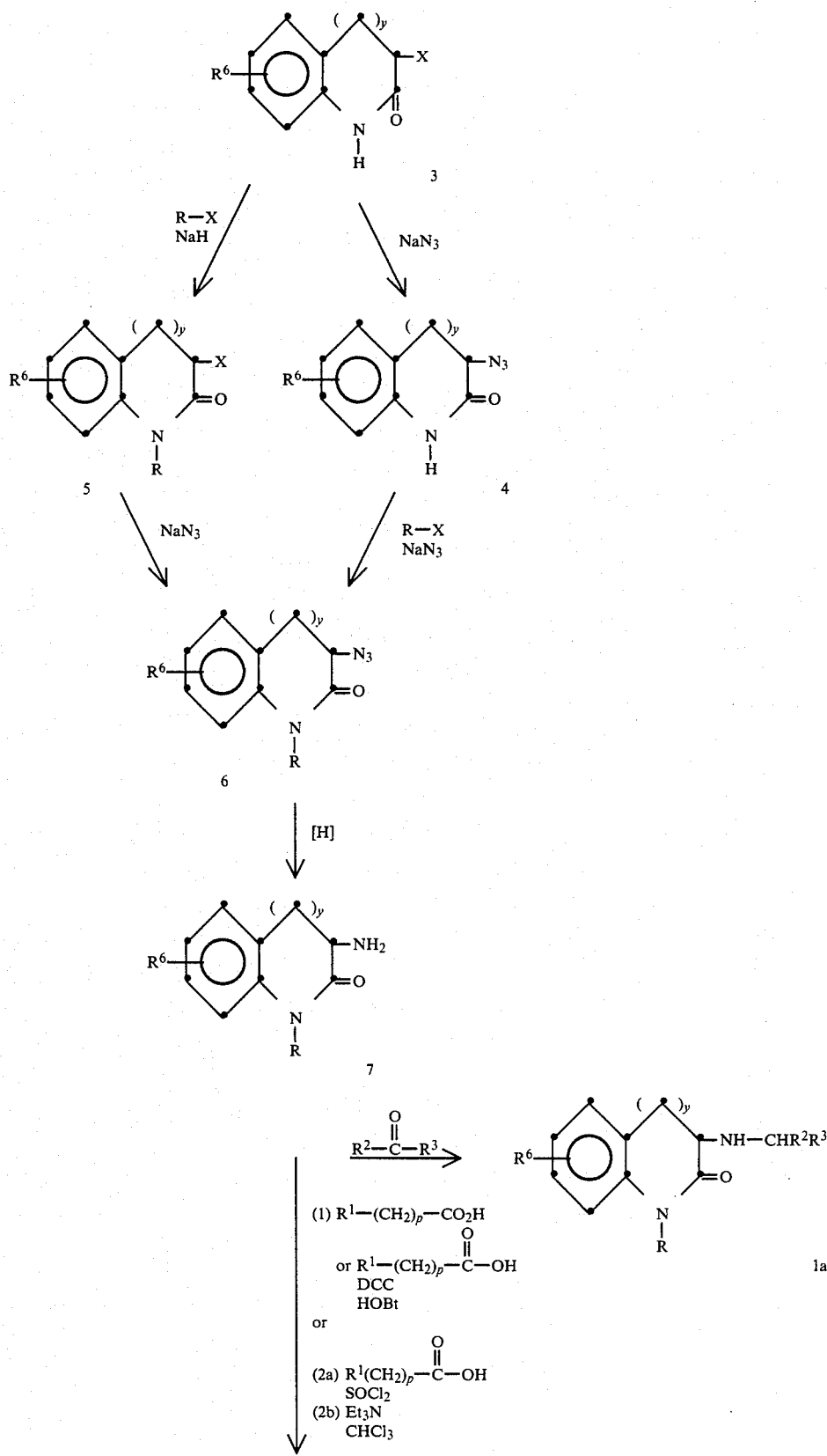

-continued
REACTION SCHEME

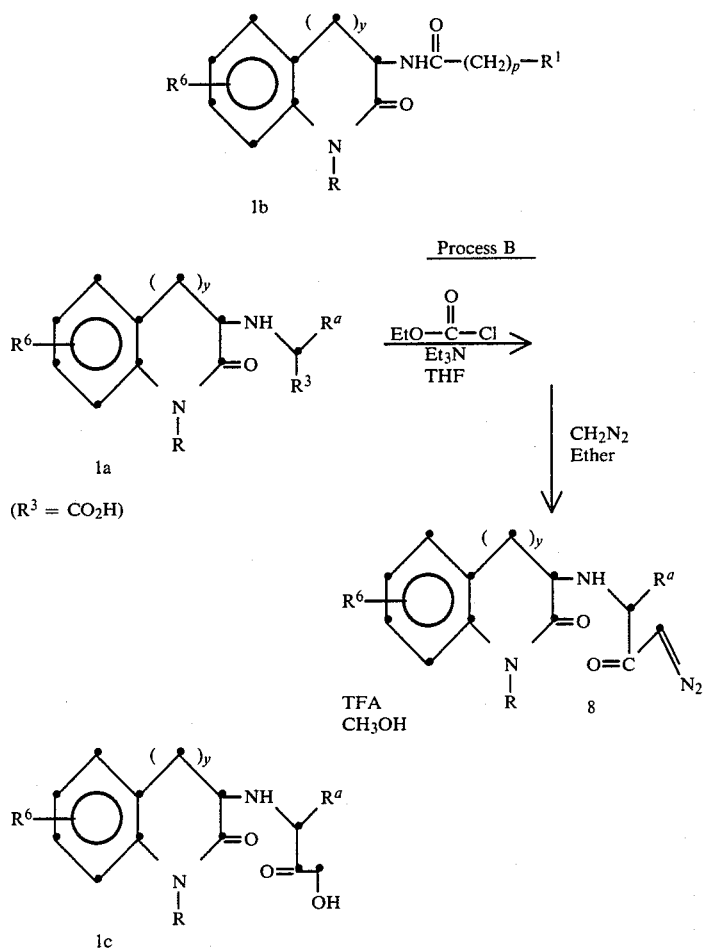

Process A

Benzofused lactam 2 ring size ranging from 6 to 8, prepared from a precursor ketone by a procedure of Blicke et al., *J. Am. Chem. Soc.*, 76, 2317 (1954), is converted to (3), with PX$_5$ where X=Br or Cl [Nagasawa et al., *J. Med. Chem.*, 14, 501 (1971)]. Reaction of (3) with sodium or lithium azide in a suitable solvent such as DMF or ethanol [see, for example, Brenner et al., *Helv. Chem. Acta*, 41, 181 (1958)] affords (4) which can be alkylated with an alkylhalide or iodoalkylester in the presence of a strong base, like sodium hydride, in a solvent such as DMF or THF to produce (5). Reduction of (5) with hydrogen and a suitable catalyst, such as palladium on carbon, affords (6).

Alternatively, (3) may be alkylated in the presence of a strong base, like sodium hydride, and the intermediate (6) converted to (7) by reaction with an azide salt as described above.

Intermediate 7 may be reductively coupled with an aldehyde, ketone, keto acid or ketoester in a solvent such as ethanol using a catalyst such as palladium on carbon to afford 1a (X=absent). 1a may also be prepared using sodium cyanoborohydride to effect reduction.

Alternatively, intermediate 7 may be coupled with a carboxylic acid using a coupling agent such as dicyclohexylcarbodiimide (DCC) and an activator such as 1-hydroxybenzotriazole (HOBt) in an aprotic solvent such as chloroform or THF to afford

Compound 1b can also be prepared by reacting 7 with an acid chloride and a tertiary amine such as triethylamine in an aprotic solvent such as chloroform or THF. The acid chloride is prepared from a carboxylic acid and thionyl chloride or PCl$_3$ in an aprotic solvent such as chloroform.

The compounds claimed may also be prepared as their R- or S-enantiomers, chiral at the C-3 amino group by resolution of compounds of structure 7 with resolving agents, such as D- or L-tartaric acid, in a solvent, such as acetone. After recrystalization of the resulting salt in solvents, such as ethanol, the free amine is isolated by dissolving the salt in water and adjusting the pH to 9 with ammonium hydroxide. The free amine is extracted from water with a solvent, such as methylene chloride. Claimed compounds may then be prepared via procedures outlined above.

Process B

Compound 1*a* (R$^3$=CO$_2$H) may be further elaborated as follows. The acid 1a can be reacted with an alkoxychloroformate (such as ethylchloroformate), a tertiary amine (such as triethylamine) in an aprotic solvent such as tetrahydrofuran (THF) to give, upon filtration, a mixed anhydride intermediate which is then reacted with an excess of diazomethane in ether to give diazomethylketone (8). Reaction of (8) with trifluoroacetic acid (TFA). Followed by stirring in methanol or ethanol gives hydroxymethyl ketone $$(R^3-\underset{\underset{O}{\|}}{C}-CH_2-OH).\quad 1c$$

In the above preparations, the keto acid or ester can be represented by the formula

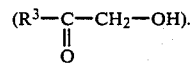

and may be, for example, 2-oxo-4-phenyl-butyric acid. Other α-keto acids or esters may be utilized to prepare other compounds of the present invention for various definitions of $R^a$ and Y. Such α-keto acids are readily available or may be prepared by well-known techniques. For example, synthons such as

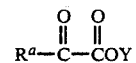

can be converted to α-keto acids or esters using methods involving alkylation followed by hydrolysis as described in the literature. An excellent method involves the reaction of Grignard reagents $R^aMgX$ with ClCO-CO$_2$Y or YO$_2$CCO$_2$Y. Another method involves condensing substituted acetic acid esters with diethyl oxalate followed by hydrolytic decarboxylation under acidic conditions to obtain α-keto acids. Carefully controlled acid hydrolysis in alcohol of acyl cyanides, which are prepared from acid chlorides and cuprous cyanide, also proves to be a viable synthetic route to α-keto esters. Nucleophilic displacement reactions on chloro or bromo pyruvic acid (ester) can also be used to produce a variety of interesting α-keto acids (esters). In these formulae, Y is a group such as loweralkyl or benzyl.

Additional compounds of Formula I can be prepared by employing the keto acids and esters listed in Table I below.

TABLE I

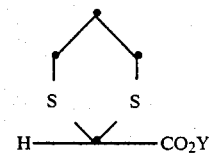

| Keto Acids and Esters of the Formula | $R^a-\underset{\underset{COOY}{\|}}{C}=O$ |
|---|---|
| (a) | ⬡—CH$_2$CH$_2$COCOOH |
| (b) | ⬡—CH$_2$CH$_2$COCOOC$_2$H$_5$ |

TABLE I-continued

| Keto Acids and Esters of the Formula | $R^a-\underset{\underset{COOY}{\|}}{C}=O$ |
|---|---|
| (c) | ⬡—CH$_2$CH$_2$COCOOCH$_2$C$_6$H$_5$ |
| (d) | ⬡—CH$_2$CH$_2$CH$_2$COCOOC$_2$H$_5$ |
| (e) | Cl—⬡—CH$_2$COCOOH |
| (f) | indole—CH$_2$CH$_2$COCOOC$_2$H$_5$ |
| (g) | thienyl—CH$_2$CH$_2$COCOOH |
| (h) | pyridyl—CH$_2$CH$_2$COCOOC$_2$H$_5$ |
| (i) | quinolinyl—CH$_2$CH$_2$COCOOH |
| (j) | HO—⬡—CH$_2$CH$_2$COCOOH |
| (k) | Cl-substituted ⬡—CH$_2$CH$_2$COCOOH |
| (l) | O$_2$N—⬡—CH$_2$CH$_2$COCOOC$_2$H$_5$ |

(precursor for the corresponding amino compound)

TABLE I-continued

Keto Acids and Esters of the Formula $\overset{R^a-C=O}{\underset{COOY}{|}}$ (m) 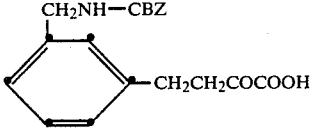

(precursor for the corresponding amino compound)

(n) 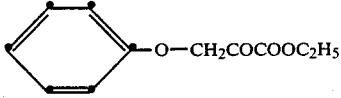

(o) 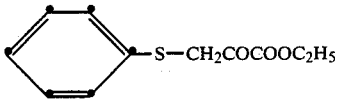

(p) CH₃S—CH₂CH₂COCOOH
(q) (CH₃)₂—CH₂CH₂COCOOH
(r) CBZ—HN(CH₂)₄—COCOOH
(precursor for the corresponding amino compound)

(s) 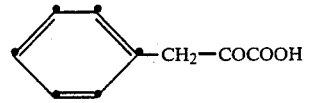

(t) 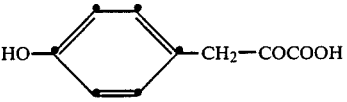

(u) 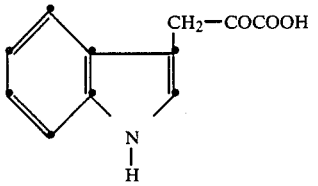

The following examples set forth the best mode currently known for preparing the compounds of the invention and are not intended to be construed as limitative, but rather illustrative, thereof. Unless otherwise indicated, all temperatures are in degrees Celcius.

EXAMPLE 1

Preparation of
1-Methyl-3-(1-carboethoxy-3-phenyl-1-propyl)amino-bromodihydrocarbostyril A. 3-Bromo-homodihydrocarbostyril (3-bromo-2,3,4,5-tetrahydro-1H-(1)benzazepin-2-one)

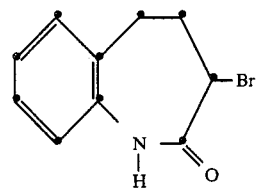

To a solution of 15 gm (0.093 mol) of homo dihydrocarbostyril (L. H. Briggs, J.C.S., 456 (1937)) in 200 ml of chloroform was added, in increments over a period of an hour, 19 gm of PCl₅, at which time 140 mg of iodine was added, followed by a slow, dropwise addition of 90 ml of a 1M solution of bromine in chloroform. The reaction mixture was warmed to room temperature, and stirring was continued an additional one hour.

The crude reaction mixture was concentrated in vacuo and partitioned between water, ice and chloroform. The aqueous layer was extracted 2 times with methylene chloride and the combined organic fractions were filtered through MgSO₄ and concentrated in vacuo. The crude bromide was chromatographed (silica, 2:1 ether:hexanes) to give 6.5 gm of pure 3-bromo-homodihydrocarbostyril.

TLC (silica, 2:1 ether:hexanes) $R_f$=0.65.
NMR (CDCl₃, TMS) 2.4–3.0 (m, 4H); 4.4–4.7 t, 1H); 7.2 (s, 4H); 9.2 (bs, 1H).
IR 1650 cm$^{-1}$.
Mass spectrum: M+ 239, m/e: 241 (M+, +2); 160 (M+²—Br); 132 (—C=O).

B. 3-Azido homodihydrocarbostyril

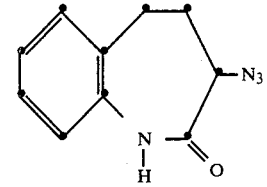

To a solution of 9.98 gm (0.0417 mol) of 3-bromo homodihydrocarbostyril in 200 ml of DMF was added 10.8 gm of sodium azide stirring 12 hours at 60° C. at which time the DMF was removed at reduced pressure. To the crude reaction mixture was added 50 ml of water and the mixture was then extracted 3 times with 50 ml of chloroform. The combined organic fractions were washed with 25 ml of a saturated solution of NaCl, filtered through MgSO₄ and concentrated at reduced pressure. Chromatography (silica, 2:1 ether:hexanes) gave 7.92 gm of pure 3-azido homodihydrocarbostyril. m.p. 150°–151° C.

TLC (silica, 2:1 ether:hexanes) $R_f$=0.71.
El. An. Calc. for C₁₀H₁₀N₄O: N, 27.71; C, 59.39; H, 4.98. Found: N, 27.27; C, 59.25; H, 4.98.
NMR (CDCl₃, TMS) 2.2–2.8 (m, 4H), 3.6–4.0 (dd, 1H); 7.2 (bs, 4H) 9.2 (bs, 1H) IR N₃ 2130, CO 1678.
Mass spectrum: M+ 202, m/e 174 (M+—N₂; 146 (C=O).

C. 3-Azido-1-methylhomodihydrocarbostyril

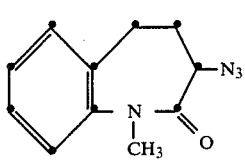

To a suspension of 151 mg of sodium hydride (50% dispersion in oil washed 3 times with hexanes) in 3 ml of THF at 0° C. was added dropwise a solution of 0.6 gm of 3-azidohomodihydrocarbostyril and 0.37 ml of methyl iodide in 3ml of THF. The reaction was carefully monitored by tlc (silica, 7:3 hexane:ethyl acetate) until reaction was complete at which time it was quenched with 10 ml of saturated NH₄Cl, diluted with 10 ml of H₂O and extracted 2 times with 10 ml of ethyl acetate. The combined organic layers were filtered through MgSO4, concentrated in vacuo and chromatographed (silica, 7:3, hexane:ethyl acetate) to give 0.45 gm of product.

NMR (CDCl3, TMS) 2.0–3.1 (m, 4H); 3.4 (S, 3H); 3.5–3.8 (overlapping d, 1H); 7.2 (S, 4H).

D. 3-Amino-1-methylhomodihydrocarbostyril

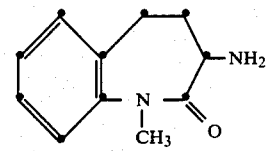

A solution of 2.7 gm of 3-azido-1-methyl homodihydrocarbostyril in 18 ml of absolute ethanol with 0.27 gm of pd/C 10% was hydrogenated for 12 hours at room temperature and 40 lbs of H2. The reaction was subsequently filtered and the ethanol removed at reduced pressure to give 2.6 gm of amine.

NMR (CD3OD, TMS) 1.8–3.0 (m, 4H); 3.4 (S, 3H); 3.4–3.8 (M, 1H); 7.2 (M, 4H).

E. 1-Methyl-3-(1-Carboethoxy-3-phenyl-1-propyl)aminohomodihydrocarbostyril

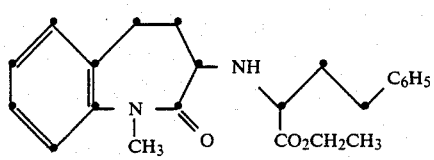

A solution of 2.6 gm of 1-methyl-3-amino homodihydrocarbostyril 8.65 gm of ethyl-4-phenyl-2-oxobutyrate and 0.72 gm of acetic acid in 15 ml of absolute ethanol was stirred 1 hour at room temperature. To the stirred solution was added dropwise over a 16 hour period a solution of 1.9 gm of NaCNBH3 in 12 ml of ethanol. After stirring a further 8 hours, the reaction was concentrated and partitioned between H2O and ethylacetate. After extracting twice with ethyl acetate the combined organic layers were filtered through MgSO4, concentrated in vacuo and chromatographed (silica, 7:3, hexane:ethylacetate) to give two diasteriomeric racemates.

Racemate A 440 mg.

TLC (silica, 7:3, hexane:ethylacetate) $R_f=0.21$.

NMR (CDCl3, TMS) 1.2 (t, 3H; 1.6–3.2 (m, 11H); 3.4 (s, 3H); 4.15 (q, 2H); 7.1–7.3 (overlapping singlets; 9H).

El. An. Calc. for $C_{23}H_{28}O_3N_2.0.025H_2O$: N, 7.28; C, 71.75; H, 7.33. Found: N, 7.22; C, 72.06; H, 7.44.

Racemate B 520 mg.

TLC (silica, 7:3, hexane:ethylacetate) $R_f=0.15$.

NMR (CDCl3, TMS) 1.1 (t, 3H); 1.6–3.5 (m, 11H); 3.3 (S, 3H); 4.0 (q, 2H); 7.15 (S, 9H).

El. An. Calc. for $C_{23}H_{28}O_3N_2.0.5H_2O$: N, 7.19; C, 70.93; H, 7.25. Found: N, 7.15; C, 71.33; H, 7.35.

EXAMPLE 2

Preparation of 1-carbomethoxymethyl-3-(3-indole methyl)amino homodihydrocarboxtyril A. 1-t-butoxycarbonylmethyl-3-azido homodihydrocarbostyril

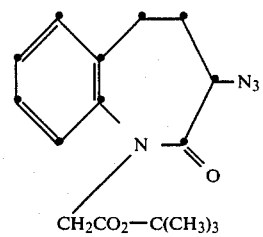

To a suspension of 1 gm of sodium hydride (50% dispersion in oil washed 3 times with hexanes) in 20 ml of THF at 0° C. was added dropwise a solution of 4.2 gm (0.02 mol) of 3-azido homodihydrocarbostyril (Compound B, Example 1) and 3 ml of t-butyliodo acetate in 20 ml of THF. The reaction was carefully monitored by TLC (silica, 2:1 ether:hexanes) until reaction was complete at which time the reaction was quenched with 30 ml of saturated NH4Cl, diluted with 20 ml H2O and extracted 3 times with 50 ml CH2Cl2. The combined organic layers were filtered, concentrated in vacuo and chromatographed (silica, 2:1 ether:hexanes) to give 4.5 gm of pure 1-t-butoxycarbonylmethyl-3-azido homodihydrocarbostyril.

m.p 103°–104° C. TLC (silica, 2:1 ether:hexanes) $R_f=0.74$.

El. An. Calc. for $C_{16}H_{20}N_4O_3$:N, 17.71; C, 60.74; H, 6.37. Found: N, 17.39; C, 60.54; H, 6.61.

NMR (CDCl3, TMS) 1.5 (s, 9H), 2.2–3.4 (m, 4H); 3.5–4.0 (overlapping doublets, 1H); 4.2–4.8 (ABq, 2H); 7.2 (s, 4H).

Mass spectrum: $M^+$ 316, m/e 288 ($M^+$—$N_2$; 260 ($M^+$—$C_4H_9$).

B. 1-t-butoxycarbonylmethyl-3-aminohomodihydrocarbostyril

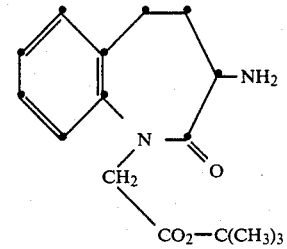

A solution of 8.01 gm of 1-t-butoxycarbonylmethyl-3-azidohomodihydrocarbostyril in 150 ml of absolute ethanol with 0.8 gm of Pd/C 10% was hydrogenated for 12 hr at room temperature and 40 lbs of H2. The reaction was subsequently filtered and the ethanol removed at reduced pressure to give 7.05 gm of pure 1-t-butoxycarbonylmethyl-3-aminohomodihydrocarbostyril.

m.p. 107°–109° C.

El. An. Calc. for $C_{16}H_{22}N_2O_3.0.5H_2O$: N, 9.36; C, 64.19; H, 7.41. Found: N, 9.18; C, 64.17; H, 7.53.

NMR ($D_aO$, CDCl3, TMS) 1.4 (s, 9H), 2.2–3.8 (m, 5H); 4.1–4.7 (ABq, 2H); 7.05 (bs, 4H).

IR C=O 1735, 1660.

Mass spectrum: $M^+$ 290, m/e 262 ($M^+$—C=O); 234 ($M^+$—$C_4H_8$); 217 ($M^+$—$C_4H_9O$).

C. 1-carbomethoxymethyl-3-aminohomodihydro carbostyril

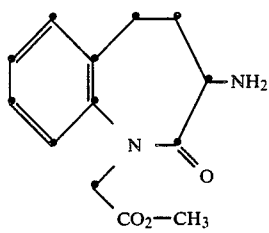

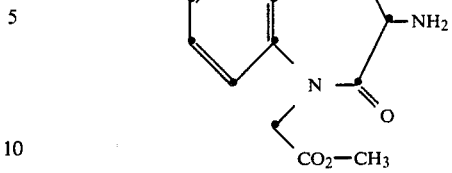

A solution of 1 gm of 1-t-butoxycarbonylmethyl-3-aminohomodihydrocarbostyril in 20 ml of methanol was saturated with HCl, the flask was sealed and the reaction allowed to stir 5 hours at room temperature. The reaction mixture was concentrated in vacuo and partitioned between dilute NaHCO$_3$ and ethylacetate. The H$_2$O layer was extracted 2 times with ethylacetate and the combined organic layers were filtered through MgSO$_4$ and concentrated at reduced pressure to give 850 mg of product.

NMR (CDCl$_3$, TMS) 1.8–3.6 (m, 7H); 3.65 (S, 2H), 4.5 (ABq, 2H); 7.1 (S, 4H).

D. 1-Carbomethoxymethyl-3-(3-indolemethyl)amino homodihydrocarboxtyril

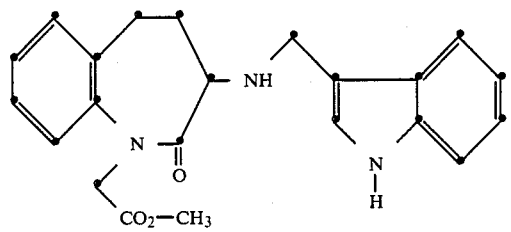

A solution of 0.5 gm of 1-carbomethoxymethyl-3-aminohomodihydrocarbostyril, 0.87 gm of Indole-3-carboxaldehyde and 0.12 ml of acetic acid in 6 ml of methanol was stirred 1 hour at room temperature. To the stirred solution was added dropwise over 6 hours a solution of 0.32 gm of NaCNBH$_3$ in 6 ml of methanol. After stirring an additional 8 hours, the reaction was concentrated in vacuo, and partitioned between H$_2$O and ethylacetate. The organic layer was filtered through MgSO$_4$, concentrated and chromatographed (silica, 9:1:1, ethylacetate:acetonitrile:methanol) to give 0.16 gm of said product.

TLC (silica, 9:1:1, ethylacetate:acetonitrile:methanol) R$_f$=0.36.

NMR (CDCl$_3$, TMS) 1.8–3.6 (m, 6H); 3.7 (s, 3H); 3.8 (ABq, 2H); 4.6 (s, 2H); 6.9 (m, 1H); 7.1 (bs, 7H); 7.5–7:7 (m, 1H); 8.4 (bs, 1H).

EXAMPLE 3

Preparation of 1-carbomethoxymethyl-3-[1-(2-hydroxy-1-oxoethyl)-3-phenyl-1-propyl]aminohomodihydrocarbostyril A. 1-carbomethoxymethyl-3-aminohomodihydrocarbostyril A solution of 1 gm of 1-t-butoxycarbonylmethyl-3-aminohomodihydrocarbostyril (Compound B, Example 2) in 20 ml of methanol was saturated with HCl, the flask sealed and the reaction allowed to stir 6 hours at room temperature. The reaction mixture was concentrated in vacuo and partitioned between dilute NaHCO$_3$ and ethylacetate. The H$_2$O layer was extracted 2 times with ethylacetate and the combined organic layers were filtered through MgSO$_4$ and concentrated at reduced pressure to give 850 mg of product.

NMR (CDCl$_3$, TMS) 1.8–3.6 (m, 7H); 3.65 (s, 2H), 4.5 (ABq, 2H); 7.1 (s, 4H).

B. 1-carbomethoxymethyl-3-(1-t-butoxycarbonyl;-3-phenyl-1-propyl)-aminohomodihydrocarbostyril (Racemate mixture)

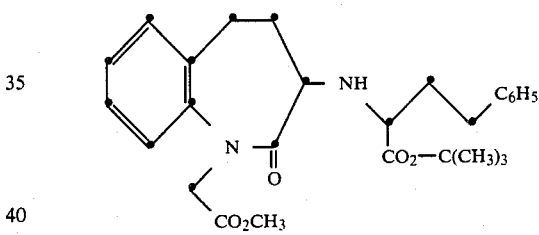

A solution of 4.3 gm of 1-carbomethoxymethyl-3-aminohomodihydrocarbostyril, 8 gm of t-butyl-4-phenyl-2-oxobutyrate and 1 gm of acetic acid in 35 ml of ethanol was stirred 1 hour at room temperature. To the stirred solution was added dropwise over a 10 hour period a solution of 2.67 gm of NaCNBH$_3$ in 35 ml of ethanol. After stirring for an additional 9 hours, the reaction was concentrated in vacuo and partitioned between H$_2$O and ethylacetate. After extracting twice with ethylacetate the combined organic layers were filtered through MgSO$_4$, concentrated and chromatographed (silica, 1:1 ethylacetate:hexanes) to give two diasteriomeric racemates of which racemate B was retained.

Racemate B 3 gm.

TLC (silica, 1:1 ethylacetate:hexanes) R$_f$=0.64.

NMR (CDCl$_3$, TMS) 1.2 (s, 9H); 1.5–3.2 (m, 11H); 3.5 (s, 3H); 3.4 (ABq, 2H); 7.0 (s, 9H).

El. Ann Calc. for C$_{27}$H$_{34}$N$_2$O$_5$: N, 6.00; C, 69.50; H, 7.35. Found: N, 5.84; C, 69.52; H, 7.27.

C. 1-Carbomethoxymethyl-3-(1-carboxy-3-phenyl-1-propyl)-aminohomodihydrocarbostyril

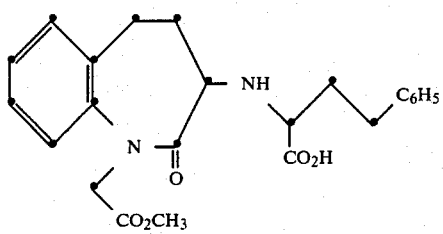

A solution of 2.5 gm of 1-carbomethoxymethyl-3-(1-t-butoxycarbonyl-3-phenyl-1-propyl)-aminohomodihydrocarbostyril, racemate B, in 20 ml of trifluoroacetic acid was stirred 12 hours at room temperature where upon it was concentrated in vacuo to yield 1.69 gm of the title compound.

NMR (CD$_3$OD, tms) 2.0–3.2 (m, 8H); 3.6 (s, 3H); 3.6–4.1 (m, 2H); 3.6 (s, 2H); 7.1–7.4 (overlapping s, 9H).

D. 1-carbomethoxymethyl-3-(1-diazodomethylcarbonyl-3-phenyl-1-propyl)-aminohomodihydrocarostyril

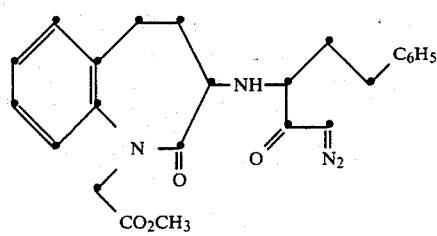

To a solution of 1.54 gm of 1-carbomethoxymethyl-3-(1-carboxy-3-phenyl-1-propyl)aminohomodihydrocarbostyril in 15 ml of THF at 0° C. was added with stirring 0.56 ml of triethylamine followed by 0.32 ml of methylchloroformate. Stirring at 0° C. was continued for 15 minutes whereupon the reaction mixture was filtered in a nitrogen atmosphere to remove precipitated triethylaminehydrochloride. To the filtrate at 0° C. was added a solution of diazomethane in ether. The reaction's progress was monitored by tlc (silica, 1:1 hexane:ethylacetate) and diazomethane solution was added as needed. When the reaction was complete (10 hours), the solution was filtered and solvents removed at reduced pressure. The crude product was purified by chromatography (silica, 1:1, hexane:ethylacetate) to give 1.25 gm of diazoketone.

TLC (silica, 1:1, hexane:ethylacetate) R$_f$=0.50.

NMR (CDCl$_3$, TMS) 1.7–3.1 (m, 8H); 3.6 (s, 3H); 3.9–4.1 (m, 2H) 4.5 (ABq, 2H); 5.5 (s, 1H); 7.1–7.3 (overlapping singlets, 9H).

E. 1-carbomethoxymethyl-3-[1-(2-hydroxy-1-oxoethyl)-3-phenyl-1-propyl]aminohomodihydrocarbostyril

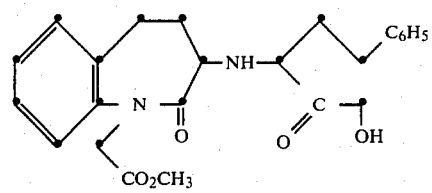

A solution of 0.3 gm of 1-carbomethoxymethyl-3-(1-(diazodomethylcarbonyl-3-phenyl-1-propyl)aminohomodihydrocarbostyril in 5 ml of trifluoroacetic acid was stirred at room temperature for 3 hours at which time the acid was removed at reduced pressure. The crude reaction mixture was dissolved in 5 ml of methanol an the solution stirred 6 hours at room temperature, where upon the methanol was removed in vacuo. The crude product was purified by chromatography (silica, 1:1, ethylacetate:hexane) to give the title compound.

TLC (silica, 1:1, ethylacetate:hexane) R$_f$=0.44.

NMR (CDCl$_4$, TMS) 1.7–3.2 (m, 11H); 3.6 (s, 3H); 4.0–5.0 (m, 5H); 7.2 (bs, 9H).

Mass spectrum: M$^+$424, m/e: 423 (M$^+$−1), 365 M$^+$−CO$_2$CH$_3$).

EXAMPLE 4

Preparation of 1-t-butoxycarbonylmethyl-3-(D-N-acetyltryptophanyl)-aminohomodihydrocarbostyril

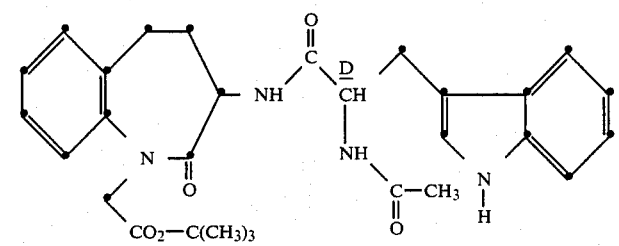

To a solution of 0.3 gm of 1-t-butoxycarbonylmethyl-3-aminohomodihydrocarbostyril (Compound B, Example 2) and 0.25 gm of N-acetyl-D-tryptophan in 5 ml of chloroform at room temperature was successively added 0.15 gm of 1-hydroxybenzotriazole and 0.24 gm of dicyclohexylcarbodiimide. After stirring for 12 hours at room temperature the reaction mixture was filtered and the filtrate was washed with H$_2$O, filtered through MgSO$_4$ and concentrated in vacuo. The product was chromatographed to give two diasteriomeric racemates.

Racemate A 150 mg.

TLC (silica, 9:1 ethylacetate:acetonitrile) R$_f$=0.416.

NMR (CDCl$_3$, TMS) 1.4 (s, 9H); 1.9 (s, 3H); 2.3–3.3 (m, 6H); 3.9–4.7 (m, 2H); 4.3 (ABq, 2H); 6.4–6.6 (overlapping d, 2H); 6.9–7.5 (m, 9H); 8.6 (bs, 1H).

Racemate B 200 mg.

TLC (silica, 9:1, ethylacetate:acetonitrile) R$_f$=0.416.

NMR (CDCl$_3$, TMS) 1.35 (s, 9H), 1.8 (s, 3H); 2.1–3.3 (m, 6H); 4.3 (ABq, 2H); 4.0–4.8 (m, 2H); 6.3–6.7 (overlapping d, 2H); 6.8–7.5 (m, 9H); 8.5 (bs, 1H).

EXAMPLE 5

Preparation of
1-t-butoxycarbonylmethyl-3-(L-N-acetyltryptophanyl)-aminohomodihydrocarbostyril

EXAMPLE 6

Preparation of
1-t-butoxycarbonylmethyl-3(L-N-carbobenzyloxytryptophanyl)aminohomodihydrocarbostyril

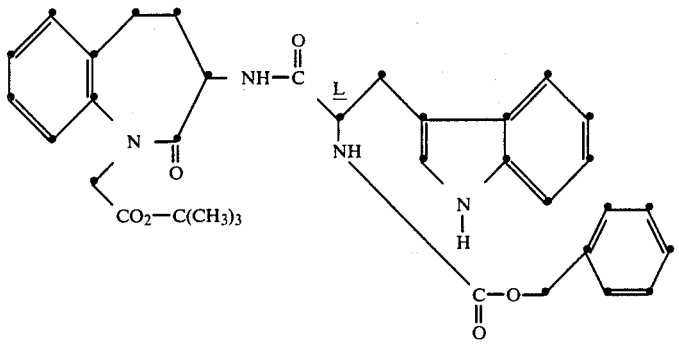

To a solution of 0.3 gm of 1-t-butoxycarbonylmethyl-3-aminohomodihydrocarbostyril (Compound B, Example 2) and 0.36 gm of N-carbobenzyloxy-L-tryptophan in 5 ml of chloroform at room temperature was successively added 0.15 gm of 1-hydroxybenzotriazole and 0.24 gm of dicyclohexylcarbodiimide. After stirring for 4 hours the reaction mixture was filtered, concentrated in vacuo and chromatographed to give two diasteriomeric racemates.

Racemate A 100 mg
TLC (silica, 1:1 ethylacetate:hexane) R$_f$=0.27.
NMR (CDCl$_3$, TMS) 1.65 (s, 9H); 1.8–3.4 (m, 6H); 4.35 (ABq, 2H); 4.1–4.6 (m, 2H); 5.1 (s, 2H); 5.5 (d, 1H); 6.6 (d, 1H); 6.8–7.6 (m, 14H); 8.3 (s, 1H).

Racemate B 130 mg.
TLC (silica, 1:1, ethylacetate:hexane) R$_f$=0.27.
NMR (CDCl$_3$, TMS) 1.4 (s, 9H), 1.7–3.3 (m, 6H); 4.35 (ABq, 2H); 4.2–4.6 (m, 2H); 5.0 (s, 2H); 5.4 (d, 1H); 6.7 (d, 1H); 6.8–7.4 (m, 14H); 8.4 (bs, 1H).

EXAMPLE 7

Preparation of
1-t-butoxycarbonylmethyl-3-((D)-N-carbobenzyloxytryptophanyl)aminohomodihydrocarbostyril

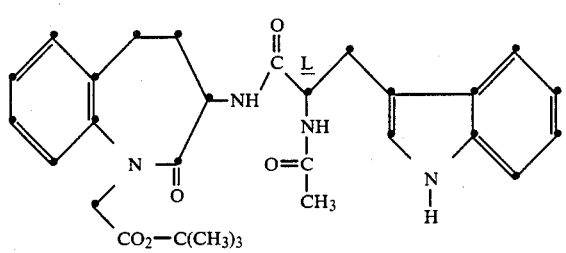

To a solution of 0.3 gm of 1-t-butoxycarbonylmethyl-3-aminohomodihydrocarbostyril (Compound B, Example 2) and 0.25 gm of N-acetyl-D-tryptophan in 5 ml of chloroform at room temperature was successively added 0.15 gm of 1-hydroxybenzotriazole and 0.24 gm of dicyclohexylcarbodiimide. After stirring for 12 hours the reaction mixture was filtered. The filtrate was washed with H$_2$O, filtered through MgSO$_4$ and concentrated in vacuo and chromatographed to give two diasteriomeric racemates.

Racemate A
TLC (silica, 9:1 ethylacetate:acetonitrile) R$_f$=0.26.
NMR (CDCl$_3$, TMS) 1.4 (s, 9H); 1.8 (s, 3H); 2.3–3.3 (m, 6H); 3.9–3.7 (m, 2H); 4.3 (ABq, 2H); 6.4–6.7 (overlapping d, 2H); 6.8–7.4 (m, 9H); 8.6 (bs, 1H).

Racemate B
TLC (silica, 9:1, ethylacetate:acetonitrile) R$_f$=0.26.
NMR (CDCl$_3$, TMS) 1.3 (s, 9H), 1.7 (s, 3H); 2.1–3.2 (m, 6H); 4.3 (ABq, 2H); 4.1–4.8 (m, 2H); 6.6–7.7 (m, 11H).

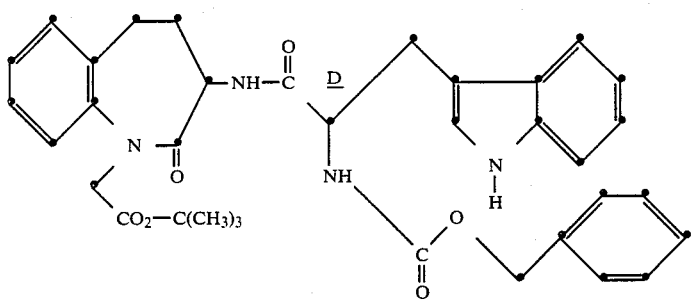

To a solution of 0.3 gm of 1-t-butoxycarbonylmethyl-3-aminohomodihydrocarbostyril (Compound B, Example 2) and 0.36 gm of N-carbobenzyloxy-D-tryptophan in 5 ml of chloroform at room temperature was successively added 0.15 gm of 1-hydroxybenzotriazole and 0.24 gm of dicyclohexylcarbodiimide. After stirring 12 hours at room temperature, the reaction mixture was filtered and partitioned between H$_2$O and chloroform. The chloroform fraction was filtered through MgSO$_4$, concentrated in vacuo and chromatographed to give two diasteriomeric racemates.

Racemate A 150 mg.

TLC (silica, 1:1 ethylacetate:hexane) $R_f=0.27$.

NMR (CDCl$_3$, TMS) 1.4 (s, 9H); 1.8-3.4 (m, 6H); 4.35 (ABq, 2H); 4.1-4.6 (m, 2H); 5.1 (s, 2H); 5.55 (d, 1H); 6.6 (d, 1H); 6.8-7.4 (m, 14H); 8.4 (bs, 1H).

Racemate B 200 mg.

TLC (silica, 1:1, ethylacetate:hexane) $R_f=0.27$.

NMR (CDCl$_3$, TMS) 1.4 (s, 9H); 2.0-3.4 (m, 6H); 4.4 (ABq, 2H); 4.2-4.6 (m, 2H); 5.1 (s, 2H); 5.55 (d, 1H); 6.8 (d, 1H); 6.8-7.5 (m, 14H); 7.6 (bs, 1H).

EXAMPLE 8

Preparation of 1-t-butoxycarbonylmethyl-3-(carbonyl-2-indolyl-)aminohomodihydrocarbostyril

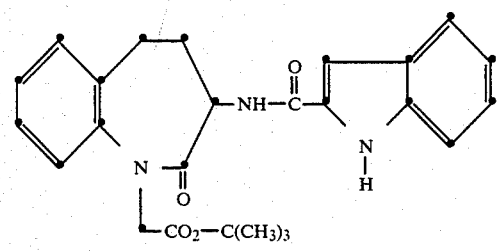

Toe a solution of indole-2-carboxylic acid 0.165 gm (0.001 mol) in 3 ml or chloroform at room temperature there was added 0.25 ml of thionyl chloride. This solution was stirred 8 hours at room temperature whereupon it was evaporated in vacuo. To a solution of the resulting acid chloride in 3 ml of chloroform there was added 1-t-butoxycarbonylmethyl-3-aminohomodihydrocarbostyril (0.3 gm, 0.001 mol) and 0.14 ml of triethylamine at room temperature. The reaction was monitored by tlc (silica, 1/1, EtOAc/hexanes). After 3 hours, the starting material had been converted to a nonpolar product. The reaction mixture was then partitioned between ethylacetate and water. After extracting the water layer with ethylacetate, the combined organic layers were dried over Na$_2$SO$_4$, filtered through MgSO$_4$, evaporated at reduced pressure and chromatographed, (silica, 2/1, hexanes/ethylacetate) to give 0.3 gm of product.

TLC (silica, 1:2, ethylacetate:hexanes) $R_f=0.77$.

NMR (CDCl$_3$, TMS) 1.5 (s, 9H0, 1.9-3.5 (m, 5H), 4.5 (ABq, m, 3H), 6.8-7.6 (m, 9H).

Mass spectrum: M$^+$433, m/e 377 (M$^+$—C$_4$H$_8$), 360 (M$^+$—C$_4$H$_9$O).

EXAMPLE 9

Preparation of 1-Carboxymethyl-3-(carbonyl-2-indolyl-)aminohomodihydrocarbostyril

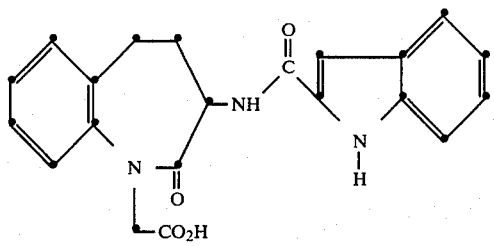

To a solution of 1-carbo-t-butoxymethyl-3-(carbonyl-2-indolyl)aminohomodihydrocarbostyril (0.2 gm) in 2 ml of chloroform at room temperature was added 2 ml of trifluoroacetic acid. The reaction was stirred 3 hours whereupon it was evaporated in vacuo to give 0.13 gm of product.

Mass spectrum: M$^+$377.

EXAMPLE 10

Preparation of 1-t-butoxycarbonylmethyl-3-(1-p-chlorobenzoyl-)aminohomodihydrocarbostyril

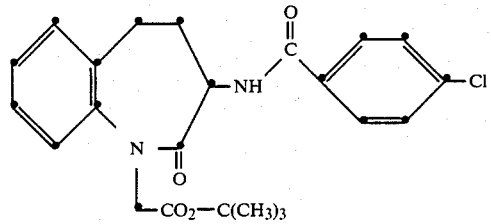

To a solution of 1-t-butoxycarbonylmethyl-3-aminohomodihydrocarbostyril (0.5 gm, 0.0017 mol) in 12 ml of methylene chloride there was added 0.297 gm of 4-chlorobenzoic acid followed by 0.25 gm of 1-hydroxybenzotriazole and 0.39 gm of dicyclohexylcarbodiimide. The reaction mixture was stirred 12 hours at room temperature whereupon it was filtered, washed with 5% Na$_2$CO$_3$, 5% citric acid, and saturated NaHCO$_3$. The solution was then filtered through MgSO$_4$, evaporated in vacuo, and chromatographed (silica, 7:3, hexanes:ethylacetate) to give 0.35 gm of product.

TLC (silica, 7:3, hexanes:ethylacetate) $R_f=0.5$.

El. An. Calc. for C$_{23}$H$_{25}$N$_2$O$_4$Cl: N, 6.53; C, 64.41; H, 5.87. Found: N, 6.07; C, 64.14; H, 5.86.

NMR (CDCl$_3$, TMS) 1.5 (s, 9H), 2.0-3.5 (m. 4H), 4.4 (ABq, 2H), 4.4-4.9 (m, 1H), 7.1-7.8 (m, 8H).

Mass spectrum: m$^+$429.

EXAMPLE 11

Preparation of
1-carboxymethyl-3-(1-p-chlorobenzoyl-)aminohomodihydrocarbostyril

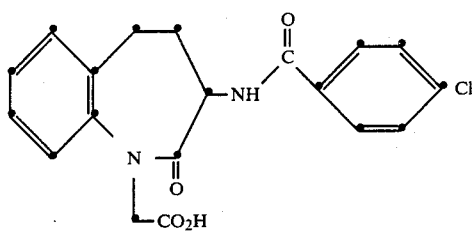

A solution of 1-carbo-t-butoxymethyl-3-(1-p-chlorobenzoyl)-aminohomodihydrocarbostyril in 5 ml of trifluoroacetic acid was stirred for 12 hours at room temperature whereupon it was evaporated in vacuo to give 0.17 gm of the title compound.

NMR (CDCl$_3$, CD$_3$OD, TMS) 2.0–3.6 (m, 4H), 4.5 (ABq, 2H), 4.6–4.9 (m, 1H), 7.1–7.8 (m, 8H).

Mass spectrum: M+375.

EXAMPLE 12

Preparation of
1-t-butoxycarbonylmethyl-3-(benzoyl)aminohomodihydrocarbostyril

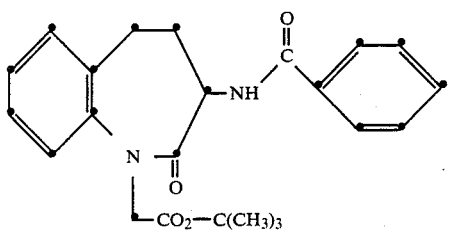

This compound (0.590 gm) was prepared from 0.4 gm of 1-t-butoxycarbonylmethyl-3-amino homodihydrocarbostyril (Example 2, Compound B), 0.185 gm of benzoic acid, 0.205 gm of 1-hydroxybenotriazole and 0.313 gm of dicyclohexylcarbodiimide by a process analogous to Example 10.

TLC (silica, 7:3, hexanes:ethylacetate) R$_f$=0.3.

El. An. Calc. for C$_{23}$H$_{26}$N$_2$O$_4$.0.25H$_2$O: N, 7.02; C, 69.24; H, 6.57. Found: N, 6.63; C, 69.68; H, 6.67.

NMR (CDCl$_3$, TMS) 1.5 (s, 9H), 2.0–3.5 (m, 4H), 4.4 (ABq, 2H), 4.5–4.9 (m, 1H), 7.1–8.2 (m, 9H).

Mass spectrum: M+ 394.

EXAMPLE 13

Preparation of
1-t-butoxycarbonylmethyl-3-(3,4-dichlorobenzoyl-)aminomodihydrocarbosytril

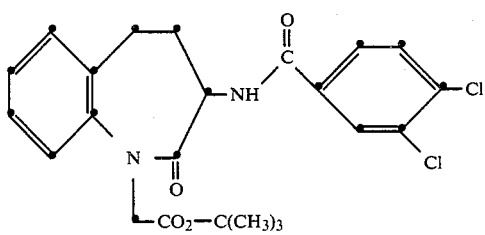

The titled compound (0.27 gm) was prepared from 0.3 gm of 1-t-butoxycarbonylmethyl-3-aminohomodihydrocarbostyril (Example 2, Compound B), 0.217 gm of 3,4-dichlorobenzoic acid, 0.15 gm of 1-hydroxybenzotriazole and 0.23 gm of dicyclohexylcarbodiimide by a process analogous to that described in Example 10.

TLC (silica, 7:3, hexanes:ethylacetate) R$_f$=0.49.

NMR (CDCl$_3$, TMS) 1.5 (s, 9H); 1.7–3.5 (m, 4H); 4.4 (ABq, 2H); 4.5–4.9 (m, 1H); 7.1–8.2 (m, 7H).

Mass spectrum: M+ 462.

EXAMPLE 14

Preparation of
1-t-butoxycarbonylmethyl-3-(4-nitrobenzoyl-)aminohomodihydrocarbostyril

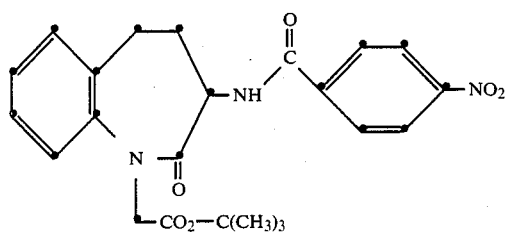

The title compound (0.29 gm) was prepared from 0.3 gm of 1-t-butoxycarbonylmethyl-3-aminodihydro carbostyril (Example 2, Compound B), 0.19 gm of 4-nitrobenzoic acid, 0.15 gm of 1-hydroxybenzotriazole and 0.23 gm of dicyclohexylcarbodiimide by a procedure analogous to that used in Example 10.

TLC (silica, 7:3, hexanes:ethylacetate) R$_f$=0.35.

NMR (CDCl$_3$, TMS) 1.5 (s, 9H); 1.8–3.4 (m, 4H), 4.5 (ABq, 2H); 4.3–4.8 (m, 1H); 7.2–8.3 (m, 8H).

Mass spectrum: M+ 410, m/c 384

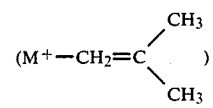

EXAMPLE 15

Preparation of
1-t-butoxycarbonylmethyl-3-(4-fluorobenzoyl-)aminohomodihydrocarbostyril

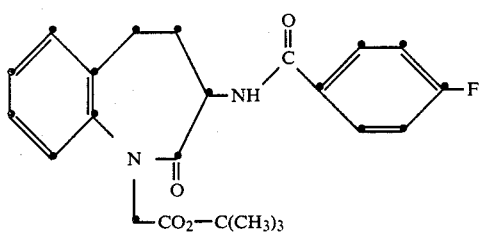

The title compound (0.38 gm) was prepared from 0.3 gm of 1-t-butoxycarbonylmethyl-3-aminohomodihydrocarbostyril (Example 2, Compound B), 0.16 gm of 4-fluorobenzoic acid, 0.15 gm of 1-hydroxybenzotriazole and 0.23 gm of dicyclohexylcarbodiimide by a procedure analogous to that employed in Example 10.

TLC (silica, 7:3, hexanes:ethylacetate) R$_f$=0.43.

NMR (CDCl₃, TMS) 1.5 (s, 9H); 1.8–3.4 (m, 4H); 4.5 (ABq, 2H); 4.4–4.8 (m, 1H); 6.7–8.2 (m, 8H).
Mass spectrum: M+ 412.

EXAMPLE 16

Preparation of 1-t-butoxycarbonylmethyl-3-(4-dimethylaminobenzoyl)aminodihydrocarbostyril

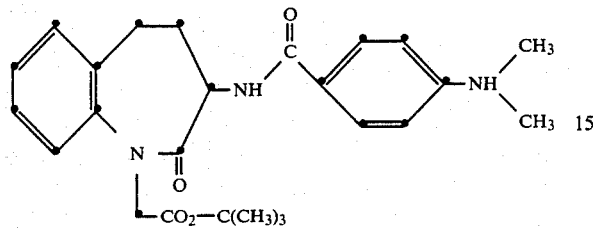

The title compound (0.2 gm) was prepared from 0.3 gm of 1-t-butoxycarbonylmethyl-3-aminohomodihydrocarbostyril (Example 2, Compound B), 0.19 gm of 4-dimethylaminobenzoic acid, 0.15 gm of 1-hydroxybenzotriazole and 0.23 gm of dicyclohexylcarbodiimide by a procedure analogous to the one employed in Example 10.

TLC (silica, 1:1, hexanes:ethylacetate) $R_f$=0.50.

NMR (CDCl₃, TMS) 1.4 (s, 9H); 1.8–3.4 (m, 4H); 2.8 (s, 6H); 4.4 (ABq, 2H); 4.4–4.8 (m, 1H); 6.8–7.4 (m, 8H).
Mass spectrum: M+ 437.

EXAMPLE 17

Preparation of t-butoxycarbonylmethyl-3-aminodihydrocarbostyril

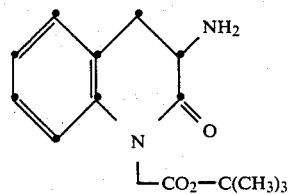

To a suspension of 2.42 gm NaH (50% oil dispersion washed 3×hexanes) in 50 ml of THF at 0° C. was added solid 5 gm (0.025 mol) of 3-aminodihydrocarbostyrilhydrochloride (T. J. McCord, Arch. of Biochem. & Biophys. 102 48, 1963) and the mixture was stirred at 0° C. until the evolution of hydrogen had ceased. When the evolution stopped, the reaction mixture was warmed to room temperature and stirred an additional 1 hour, at which time a solution of 6 gm of t-butyl iodoacetate in 20 ml of THF was added dropwise. After an additional two hours of stirring at room temperature, the reaction was quenched with 20 ml of saturated NaHCO₃, and the reaction mixture was diluted with 20 ml of H₂O and extracted twice with 50 ml of 9:1 ethylacetate:acetonitrile. The organic layers were combined, filtered through MgSO₄ and concentrated in vacuo to give 5 gm of 1-t-butoxycarbonylmethyl-3-aminodihydrocarbostyril.

NMR (CDCl₃, TMS) 1.4 (s, 9H); 2.0–3.2 (m, 4H), 3.4–3.8 (m, 1H); 4.6 (Q, 2H); 6.6–7.2 (m, 4H).
IR C=O 1738, 1680.

EXAMPLE 18

Preparation of 1-t-butoxycarbonylmethyl-3-(carbonyl-2-indolyl)aminodihydrocarbostyril

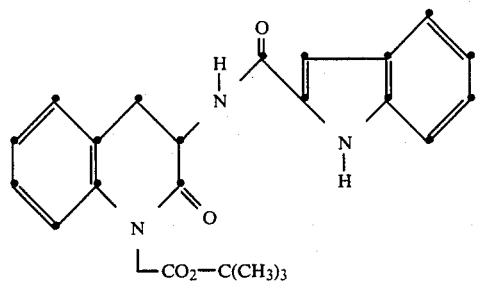

The title compound (0.35 gm) was prepared according to the procedure employed in Example 8 from t-butoxycarbonylmethyl-3-aminodihydrocarbostyril (0.4 gm) and 2-indolecarboxylic acid (0.233 gm) and thionyl chloride (0.59 ml).

TLC (silica, 7:3 hexanes:ethyl acetate) $R_f$=0.35.

NMR (CDCl₃) δ 1.5 (s, 9H), 2.95 (t, 1H), 3.7 (ABq, 1H), 4.65 (ABq, 2H), 4.75–4.9 (m, 1H), 6.9–7.2 (m, 9H).

El. An. Calc. for C₂₄H₂₅N₃O₄: N, 10.02; C, 68.72; H, 6.01: Found: N, 9.91; C, 68.46; H, 6.02.

Mass spectrum: M+ 419 m.p.: 178° C.

EXAMPLE 19

Preparation of 3-amino-1-(t-butoxycarbonylmethyl)hexahydrobenzoazocine-2-one

A. 3-bromohexahydrobenzoazocin-2-one

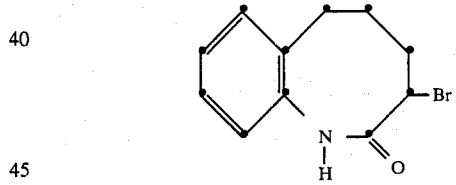

To a solution of 15 gm (0.084 mol) of hexahydrobenzoazocin-2-one (Chemica Scandinavia, 18, 191 (1964)) in 150 ml of chloroform at 0° C. was added 8.8 gm of PCl₅ in small increments over a period of an hour. To this reaction mixture was added 70 mg of iodine, followed by the slow dropwise addition of 84 ml of a 1M solution of bromine in chloroform and this reaction mixture was warmed to room temperature and stirred for 1 hour, at which time it was concentrated at reduced pressure. A mixture of ice and water was added to the crude product and the mixture was extracted three times with methylene chloride. The combined organic fractions were filtered through MgSO₄ and concentrated at reduced pressure. The solid bromide was recrystallized with a mixture of chloroform and hexanes to give 12 gm of pure 3-bromohexahydrobenzoazocin-2-one.

m.p. 194°–195° C.

TLC (silica, 2:1 ether:hexanes) $R_f$=0.36.

An. Calc. for C₁₁H₁₂NOBr.0.25H₂O: N, 5.41; C, 51.08; H, 4.68. Found: N, 5.29; C, 50.75; H, 4.53.

NMR (CDCl₃, TMS) 1.6–2.9 (m, 6H); 4.2–4.5 (bt, 1H); 7.2 (s, 4H); 8.5 (bs, 1H).

Mass spectrum: M⁺ 253, m/e: 252 (p+2, 10%); 179 (M⁺—Br); 146 (C=O).

B. 3-azidohexahydrobenzoazocine-2-one

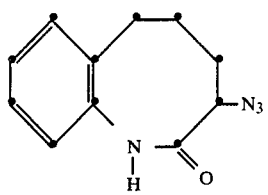

To a solution of 10 gm (0.00394 mol) of 3-bromohexahydrobenzoazocine-2-one in 100 ml of dimethylformamide (DMF) was added 10 gm of sodium azide and the resultant reaction mixture was stirred 12 hours at 60° C. The DMF was then removed at reduced pressure and the crude product was partitioned between water and methylene chloride. The aqueous layer was extracted 3 times with methylene chloride and the combined organic fractions were filtered through MgSO₄ and concentrated at reduced pressure.

The product was chromatographed (silica, 2:1 ether:hexanes) giving 8 gm of pure azide.

m.p. 142°–143° C.

TLC (silica, 2:1 ether:hexanes) R_f=0.45.

An. Calc. for C₁₁H₁₂N₄O.0.25H₂O: N, 25.36; C, 59.79; H, 5.44. Found: N, 25.17; C, 59.37; H, 5.39.

NMR (CDCl₃, TMS) 1.6–2.9 (m, 6H); 3.4–3.7 (bt, 1H); 7.2 (s, 4H); 8.5 (bs, 1H).

Mass spectrum: m/e 188, (M⁺—N₂); 159 (C=O).

C. 3-azido-1-(t-butoxycarbonylmethyl)-hexahydrobenzoazocine-2-one

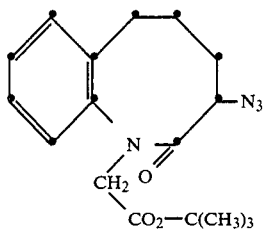

To a suspension of 1.86 gm of sodium hydride (50% suspension, prewashed with hexanes) in 40 ml THF at 0° C. was added dropwise a solution of 8 gm (0.037 mol) of azide lactam and 5.63 ml of t-butyliodo acetate in 40 ml of THF. The reaction was found to be complete upon the completion of the addition (TLC, silica gel, 2:1 ether:hexanes) and the reaction mixture was quenched by the addition of 20 ml of saturated NH₄Cl. The solution was extracted three times with 50 ml portions of ethyl acetate and the combined organic fractions were filtered through MgSO₄ and concentrated in vacuo. The crude product was purified by chromatography on silica gel using 2:1 ether:hexanes as eluant, with the fractions containing the desired product being combined and concentrated at reduced pressure to give 11 gm of 3-azido-1-(t-butoxycarbonylmethyl)-hexahydrobenzoazocine-2-one.

m.p. 120°–121° C.

TLC (silica, 2:1 ether:hexanes) R_f=0.75.

NMR (CDCl₃, TMS) 1.5 (s, 9H); 1.9–3.0 (m, 6H); 3.35–3.6 (dd, 1H); 4.0–4.6 (AB, 2H); 7.2 (s, 4H).

An. Calc. for C₁₄H₂₂N₄O₃.0.5H₂O: N, 16.50; C, 60.11; H, 6.48. Found: N, 16.39; C, 60.29; H, 6.58.

Mass spectrum: m/e 302, (M⁺—N₂); 257 (M⁺—OC₄H₉).

D. 3-amino-1-(t-butoxycarbonylmethyl)-hexahydrobenzoazocine-2-one

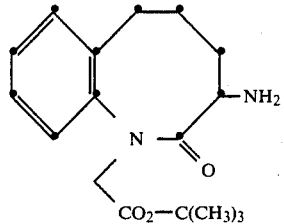

A solution of 9.5 gm (0.0287 mol) of azide lactam Q in 100 ml of absolute ethanol with 900 mg of 10% Pd/C was hydrogenated 12 hours at 40 lbs of hydrogen at room temperature. The reaction mixture was subsequently filtered and the filtrate concentrated in vacuo to give 8.7 gm of the title amine.

NMR (CDCl₃, D₂O, TMS) 1.5 (s, 9H); 1.6–2.3 (m, 4H); 2.7–2.9 (t, 3H); 3.2–3.4 (m, 1H); 4.0–4.6 (ABQ, 2H); 7.2 (s, 4H).

EXAMPLE 20

Preparation of 1-t-butoxycarbonylmethyl-3-(carbonyl-2-indolyl-)aminohexahydrobenzoazocine-2-one

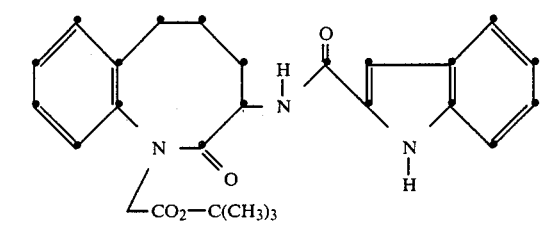

The title compound (0.6 gm) was prepared according to the method of Example 8 from t-butoxycarbonylmethyl-3-aminohexahydrobenzoazocine-2-one (0.4 gm), 2-indolecarboxylic acid (0.209 gm) and thionyl chloride (0.38 ml).

TLC (silica, 7:3 hexanes:ethyl acetate) R_f=0.32.

NMR (CDCl₃) δ 1.45 (s, 9H), 1.5–2.2 (m, 4H), 2.8–3.1 (m, 2H), 4.35 (ABq, 2H), 4.4–4.5 (m, 1H), 6.9–7.7 (m, 9H), 9.4 (s, 1H).

El. An. Calc. for C₂₆H₂₉N₃O₄.H₂O: N, 9.03; C, 67.08; H, 6.28. Found: N, 8.77; C, 67.05; H, 6.24.

Mass spectrum: M⁺ 477 m.p. 186°–188° C.

EXAMPLE 21

Preparation of 1-t-butoxycarbonylmethyl-3-(2-naphthoyl)aminohomodihydrocarbostyril

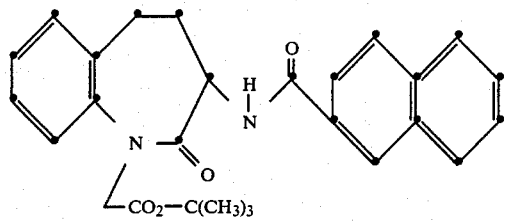

The title compound (0.15 gm) was prepared from 0.3 gm of 1-t-butoxycarbonylmethyl-3-aminohomodihydrocabostyril (Example 2, Compound B), 0.177 gm of 2-naphthoic acid, 0.14 gm of 1-hydroxybenzotriazole hydrate and 0.23 gm of dicyclohexylcarbodiimide by a procedure analogous to the procedure employed in Example 10.

TLC (silica, 7:3, hexanes/ethyl acetate) $R_f$=0.69.

NMR (CDCl$_3$) δ 1.45 (s, 9H), 2.05-2.15 (m, 1H), 2.6-2.75 (m, 1H), 2.85-3.0 (m, 2H), 3.4-3.55 (m, 1H), 4.5 (ABq, 2H), 7.2-8.3 (m, 11H).

El. An. Calc. for $C_{27}H_{28}N_2O_4$: N, 6.31; C, 72.96; H, 6.31. Found: N, 6.09; C, 72.88; H, 6.46.

Mass spectrum: M+ 444.

EXAMPLE 22

Preparation of 3(R)-amino-1-t-butoxycarbonylmethyl-2,3,4,5-tetrahydro-1H-(1)benzazepin-2-one (3(R)-amino-1-t-butoxycarbonylhomodihydrocarbostryril)

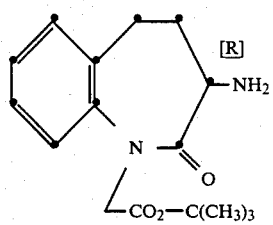

0.36 gm of the title compound was prepared from 1.4 gm of racemic starting material and 0.724 gm of D-tartaric acid by heating in 10 ml of acetone until dissolution was complete. A crystaline solid precipitated overnight and was recovered by filtration, then recrystalized twice from ethanol. This salt was dissolved in water (20 ml) and made basic to pH 9 with dilute ammonium hydroxide, and the solution was extracted with methylene chloride.

This material was dried over MgSO$_4$ and was filtered and evaporated in vacuo to give the title compound.

m.p. 111°-112° C., $(\alpha)_d$=+252° (c=1 in ethanol).

EXAMPLE 23

Preparation of 3(S)-amino-1-t-butoxycarbonylmethyl-2,3,4,5-tetrahydro-1H-(1)benzazepin-2-one (3(S)-amino-1-t-butoxycarbonylmethylhomodihydrocarbostyril)

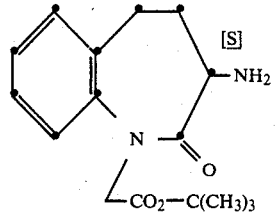

0.18 gm of the title compound was prepared from 0.5 gm of racemic starting material and 0.26 gm of L-tartaric acid by the procedure employed in Example 22.

$(\alpha)_d$= -262° C. (c=1 in ethanol).

EXAMPLE 24

Preparation of 1-t-butoxycarbonylmethyl-3(R)-(carbonyl-2-indolyl)aminohomodihydrocarbostyril

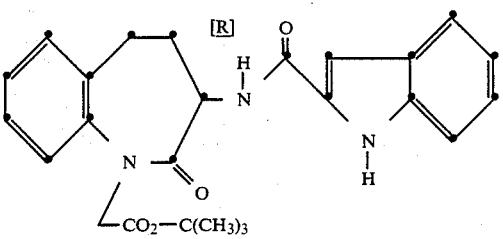

To a solution of indole-2-carboxylic acid (0.133 gm, 0.00083 mol) in chloroform (3 ml) was added 0.24 ml of thionyl chloride. This solution was stirred eight hours at room temperature, whereupon it was evaporated in vacuo. To a solution of this acid chloride in chloroform (3 ml) was added 1-t-butoxycarbonylmethyl-3(R)-aminohomodihydrocarbostyril (0.24 gm) from Example 22, and 0.12 ml of triethylamine, and after stirring for three hours, the reaction mixture was partitioned between water and ethyl acetate. After extracting the water layer with ethyl acetate, the combined organic layers were dried (MgSO$_4$) and evaporated in vacuo and chromatographed (silica, 2:1 hexanes:ethyl acetate), to give 0.2 gm of the title compound.

TLC (silica, 2:1 hexanes:ethyl acetate) $R_f$=0.4.

NMR (CDCl$_3$, TMS) δ 1.5 (s, 9H), 2.05-2.2 (m, 1H), 2.6-2.75 (m, 1H), 2.8-2.95 (m, 1H), 3.35-3.5 (m, 1H), 4.5 (ABq, 2H), 4.7-4.8 (m, 1H), 6.9-7.7 (m, 8H), 9.4 (br s, 1H).

El. An. Calc. for $C_{25}H_{27}N_3O_4$: N, 9.69; C, 69.24; H, 6.24. Found: N, 9.32; C, 69.10; H, 6.34.

$(\alpha)_d$= +141.33° (c=0.64 in ethanol) mp 119°-120° C.

Mass spectrum: M+ 433.

EXAMPLE 25

Preparation of 1-t-butoxycarbonylmethyl-3(S)-(carbonyl-2-indolyl)aminohomodihydrocarbostyril The title compound (0.24 gm) was prepared from 0.2 gm of 1-t-butoxycarbonylamino-3(S)-aminohomodihydrocarbostyril from the intermediate prepared in Example 23, and 0.11 gm of indole-2-carboxylic acid, by the procedure indicated for the preparation of the R enantiomer in Example 24.

TLC (silica, 2:1 hexanes:ethyl acetate) $R_f=0.4$.
NMR Same as for the R enantiomer mp 119°–120° C.
$(\alpha)_d = -123.3°$ (c=1.02 in ethanol).

EXAMPLE 26

Preparation of 1-t-butoxycarbonylmethyl-3(R)-(2-naphthoyl)aminohomodihydrocarbostyril The title compound was prepared from 0.1 gm 1-t-butoxycarbonylmethyl-3-(R)-aminohomodihydrocarbostyril, 0.058 gm of 2-naphthoic acid, 0.050 gm of 1-hydroxybenzotriazole hydrate, and 0.070 gm of dicyclohexylcarbodiimide, by a procedure analogous to that described in Example 10, giving 0.070 gm of product.

TLC (silica, 1:1 ethyl acetate:hexanes) $R_f=0.48$.
NMR (CDCl$_3$) 1.5 (s, 9H), 2.05–2.15 (m, 1H), 2.6–2.75 (m, 1H), 2.85–3.0 (m, 1H), 3.4–3.55 (m, 1H), 4.5 (ABq, 2H), 4.7–4.85 (m, 1H), 7.1–8.3 (m, 11H).
$(\alpha)_d = +116.78$ (c=0.28 in methanol).
Mass spectrum: M+ 444.
El. An. Calc. for C$_{27}$H$_{28}$N$_2$O$_4$: N, 6.30; C, 72.97; H, 6.30. Found: N, 5.91; C, 73.10; H, 6.36.

EXAMPLE 27

Preparation of 1-benzyl-3-(carbonyl-2-indolyl)aminohomodihydrocarbostyril

A. 3-Azido-1-benzylhomodihydrocarbostyril

To suspension of sodium hydride (0.25 gm of a 50% dispersion in oil, washed with hexanes) in tetrahydrofuran (THF) predried, 5ml) was added, dropwise, a solution of 3-azido homodihydrocarbostyril, (1 gm, 0.00495 mol) and benzyl bromide (0.589 ml, 0.00495 mol) in THF (5 ml). After two hours, TLC (silica, 7:3, hexanes:ethyl acetate) the reaction appeared to be complete and the mixture was quenched with a saturated solution of NH$_4$Cl (5 ml), diluted with water and extracted twice with ethylacetate. The combined organic extracts were dried over MgSO$_4$, filtered and reduced in vacuo. 3-Azido-1-benzylhomodihydrocarbostyril was isolated by chromatography (silica, 7:3, hexanes:ethylacetate) to give 0.98 gm.

TLC (silica, 7:3, hexanes:ethylacetate) $R_f=0.69$.
NMR (CDCl$_3$) δ 2.2–2.7 (m, 4H); 3.7–3.85 (t, 1H; 4.8–5.4 (ABq, 2H); 7.1–7.35 (m, 9H).
Mass spectrum: (FAB+) M+1 293.

B. 3-Amino-1-benzylhomodihydrocarbostyril

A solution of 3-azido-1-benzylhomodihydrocarbostyril (0.965 gm, 0.0033 mol) in ethanol (12 ml) was hydrogenated at 40 psi and room temperature for eight hours, at which time the reaction mixture was filtered and concentrated in vacuo to give 0.95 gm of 3-amino-1-benzylhomodihydrocarbostyril.

NMR (CDCl$_3$) δ 2.3–2.8 (m, 6H, NH$_2$); 3.55–3.65 (m, 1H); 4.8–5.3 (ABq, 2H); 7.1–7.35 (m, 9H).

C. 1-Benzyl-3-(carbonyl-2-indolyl)aminohomodihydrocarbostyril

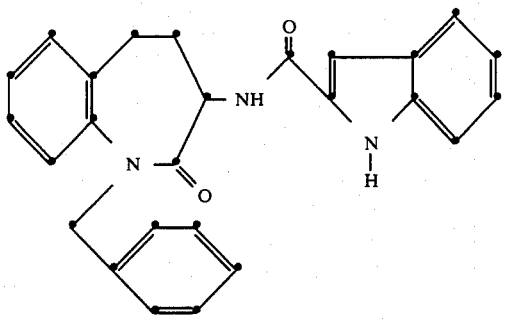

The title compound was prepared from 3-amino-1-benzylhomodihydrocarbostyril (0.5 gm, 0.0019 mol) and indole-2-carboxylic acid (0.302 gm), via the procedure outlined in Example 8. The crude product was purified by chromatography (silica, 7:3, hexanes:ethylacetate) to give the title compound.

TLC (silica, 7:3, hexanes:ethylacetate) $R_f=0.32$.

NMR (CD$_3$OD) δ 1.95–2.1 (m, 1H); 2.4–2.7 (m, 3H); 4.6–4.7 (m, 1H); 4.8–5.35 (ABq, 2H); 7.07–7.65 (m, 14H).

Mass spectrum: (FAB+) M+1,410.

EXAMPLE 28

Preparation of 1-methyl-3-(2-naphthoyl)aminohomodihydrocarbostyril

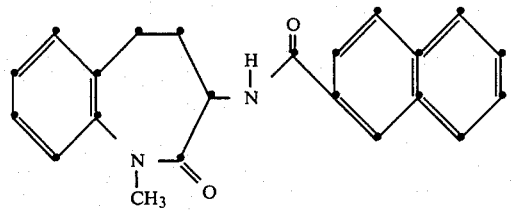

The title compound was prepared from 3-amino-1-methylhomodihydrocarbostyril (0.27 gm, 0.0014 mol) (Example 1, compound D) and 2-naphthoic acid (0.254 gm, 0.0014 mol), by the procedure outlined in Example 10. The crude product was chromatographed (silica, 1:1 ethylacetate:hexanes) to give 0.29 gm of the title compound.

TLC (silica, 1:1, ethylacetate:hexanes) $R_f=0.48$.

NMR (CDCl$_3$) δ 2.0–2.15 (m, 1H); 2.6–2.75 (m, 1H); 2.8–3.0 (m, 2H); 3.5 (s, 3H); 4.65–4.75 (m, 1H); 7.2–8.3 (m, 11H).

Mass spectrum: $M^{30}=344$.

El. An. Calc. for $C_{22}H_{20}N_2O_2$: N, 8.14; C, 76.74; H, 5.81. Found: N, 8.03; C, 76.89; H, 6.07.

EXAMPLE 29

Preparation of 1-ethoxycarbonylmethyl-3-(2-naphthoyl)aminohomodihydrocarbostyril

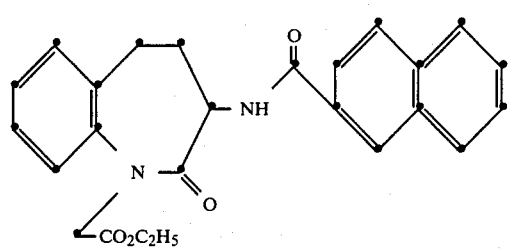

A. 1-Carboethoxymethyl-3-aminohomodihydrocarbostyril

A solution of 1-carbomethoxymethyl-3-aminohomodihydrocarbostyril (1.4 gm) in ethanol (35 ml) was cooled to 0° C. and saturated with HCl gas. This reaction mixture was sealed and stirred at room temperature for twelve hours, then concentrated in vacuo and partitioned between ethylacetate and a 10% solution of K$_2$CO$_3$. The organic fraction was dried over MgSO$_4$, filtered and concentrated in vacuo to give 1.1 gm of the title compound.

NMR (CDCl$_3$) δ 1.2–1.35 (t, 3H); 1.9–2.05 (m, 1H); 2.1–2.3 (br, s, 2H, NH$_2$); 2.4–2.55 (m, 1H); 2.55–2.7 (m, 1H); 3.2–3.35 (m, 1H); 3.45–3.55 (m, 1H); 4.2–4.3 (q, 2H); 4.4–4.7 (ABq, 2H); 7.1–7.4 (m, 4H).

B. 1-Ethoxycarbonylmethyl-3-(2-naphthoyl)aminohomodihydrocarbostyril

The title compound was prepared from 1-ethoxycarbonylmethyl-3-aminohomodihydrocarbostyril (0.4 gm, 0.0015 mol), indole-2-carboxylic acid (0.246 gm, 0.0015 mol) and thionyl chloride (0.64 ml) according to a procedure outlined in Example 8. The crude product was purified by chromatography (silica, 1:1, ethylacetate:hexanes) to give 0.133 gm of the title compound.

TLC (silica, 1:1, ethylacetate:hexanes $R_f=0.65$.

NMR (CDCl$_3$) δ 1.2–1.35 (t, 3H); 2.0–2.15 (m, 1H); 2.6–2.75 (m, 1H); 2.8–2.95 (m, 1H); 3.35–3.5 (m, 1H); 4.1–4.3 (m, 3H); 4.4–4.8 (ABq, 2H); 6.9–7.7 (m, 9H), 9.4 (br s, 1H).

Mass spectrum: (FAB+) $M^{30}1,406$.

El. An. Calc. for $C_{23}H_{23}N_3O_4.0.5H_2O$: N, 10.14; C, 66.65 H, 5.59. Found: N, 9.68: C, 66.67 H, 5.68.

EXAMPLE 30

Preparation of 1-t-butoxycarbonylmethyl-3-(2-naphthylacetyl)aminohomodihydrocarbostyril

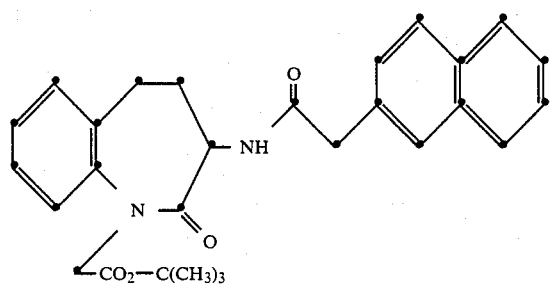

The title compound was prepared from 1-t-butoxycarbonylmethyl-3-aminohomodihydrocarbostyril (0.3 gm, 0.001 mol), 2-naphthylacetic acid (0.192 gm), 1-hydroxybenzotriazolehydrate (0.154 gm) and dicyclohexylcarbodiimide (0.234 gm) by the procedure outlined in Example 10. The crude product was chromatographed (silica, 1:1 ethylacetate:hexanes) to give 0.363 gm of the title compound.

TLC (silica, ethylacetate:hexanes, 1:1) $R_f$=0.55.

NMR (CDCl$_3$) δ 1.4 (s, 9H); 1.8∝1.9 (m, 1H); 2.5-2.75 (m, 2H); 3.25-3.35 (m, 1H); 3.7 (s, 2H); 4.15-4.64 (ABq, 2H); 4.45-4.6 (m, 1H); 6.5-6.6 (br d, 1H); 7.0-7.9 (m, 11H).

Mass spectrum: (FAB+) M+1,459.

El. An. Calc. for $C_{28}H_{30}N_2O_4 \cdot 0.25H_2O$: N, 6.05; C, 72.26; H, 6.48. Found: N, 5.80; C, 71.98; H, 6.56.

EXAMPLE 31

Preparation of 1-t-butoxycarbonylmethyl-3-(2-naphthylmethyl-)aminohomodihydrocarbostyril

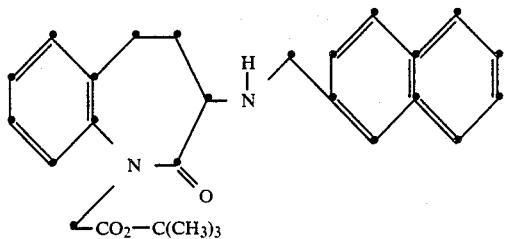

The title compound was prepared from 1-t-butoxycarbonylmethyl-3-aminohomodihydrocarbostyril (0.3 gm, 0.001 mol), 2-naphthaldehyde (0.48 gm, 0.003 mol), and NaCNBH$_3$ (0.19 gm, 0.003 mol) in methanol (6 ml) and acetic acid (0.12 ml), according to a procedure described in Example 2D. The crude product was purified by chromatography (silica, ethylacetate) to give 0.13 gm of 1-t-butoxycarbonylmethyl-3-(2-naphthylmethyl)aminohomodihydrocarbostyril.

TLC (silica, ethylacetate) $R_f$=0.48.

NMR (CDCl$_3$) 1.5 (s, 9H); 1.9-2.1 (m, 1H); 2.35-2.45 (m, 1H); 2.5-2.65 (m, 1H); 3.15∝3.3 (m, 1H); 3.3-3.34 (m, 1H); 3.55-4.0 (ABq, 2H); 4.4-4.6 (ABq, 2H); 7.1-7.8 (m, 11H).

El. An. Calc. for $C_{27}H_{29}N_2O_3$: N, 6.53; C, 75.52; H, 6.76. Found: N, 6.34; C, 75.20; H, 6.92.

Mass spectrum: (FAB+) M+1,431.

EXAMPLE 32

Preparation of 1-t-butoxycarbonylmethyl-3-(2-indolemethyl-)aminohomodihydrocarbostyril

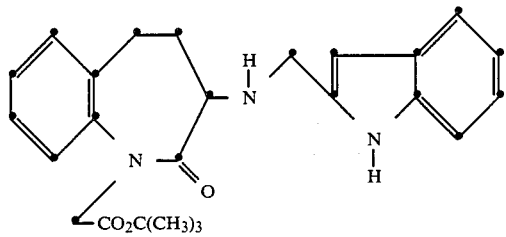

The title compound is prepared from 1-t-butoxycarbonylmethyl-3-aminohomodihydrocarbostyril, indole-2-carboxaldehyde and sodium cyanoborohydride in methanol by a procedure analogous to the one described in Example 31. The crude product is purified by chromatography on silica.

EXAMPLE 33

Preparation of 1-t-butoxycarbonylmethyl-3-(3,4-dichlorobenzyl-)aminohomodihydrocarbostyril

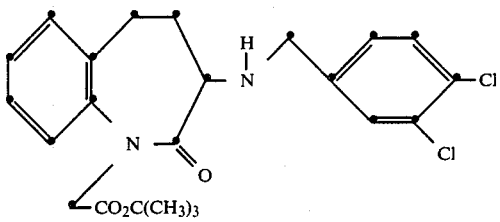

The title compound is prepared from 1-t-butoxycarbonylmethyl-3-aminohomodihydrocarbostyril, 3,4-dichlorobenzaldehyde, and sodium cyanoborohydride in methanol by the procedures described in Example 31.

What is claimed is:

1. A compound of the formula:

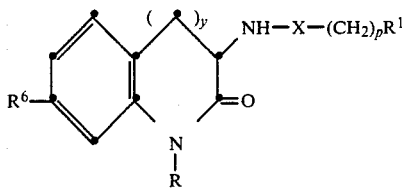

wherein:

X is absent or carbonyl;

R is unsubstituted or mono-, di-, or trisubstituted C$_1$-C$_8$-straight- or branched-alkyl, where the substituent(s) is/are selected from the group consisting of C$_1$-C$_4$-alkylthio, C$_1$-C$_4$-alkyloxy, C$_1$-C$_4$-alkylamino, unsubstituted or mono-, di-, or trisubstituted C$_6$- or C$_{10}$-aryloxy, unsubstituted or mono-, di-, or trisubstituted C$_6$- or C$_{10}$-arylthio, unsubstituted or mono-, di-, or trisubstituted C$_6$- or C$_{10}$-aryl, and unsubstituted or mono-, di-, or tri-substituted heteroaryl, and the substituent(s) on the C$_6$- or C$_{10}$-aryloxy, the C$_6$-or C$_{10}$-arylthio, the C$_6$- or C$_{10}$-aryl and the heteroaryl being selected from C$_1$-C$_8$-straight- or branched-alkyl, hydroxy, C$_1$-C$_4$-alkoxy, halo, nitro, amino, C$_1$-C$_4$-alkylthio or mono- or di-C$_1$-C$_4$-alkyl-amino; substituted carbonyl-C$_1$-C$_4$-alkyl, which carbonyl group is substituted with hydroxy, C$_1$-C$_8$-straight- or branched-alkoxy, C$_1$-C$_8$-straight- or branched-alkyl, unsubstituted or mono-, di-, or trisubstituted C$_6$- or C$_{10}$-aryl, unsubstituted or mono-, di- or trisubstituted C$_6$- or C$_{10}$-aryl-C$_1$-C$_8$-alkyl, and unsubstituted or mono-, di-, or trisubstituted C$_6$- or C$_{10}$-aryl-C$_1$-C$_4$-alkoxy, where the substituent(s) on the C$_6$- or C$_{10}$-aryl, the C$_6$- or C$_{10}$-aryl-C$_1$-C$_8$-alkyl or the C$_6$- or C$_{10}$-aryl-C$_1$-C$_4$-alkoxy is/are selected from the group consisting of hydroxy, C$_1$-C$_8$-straight- or branched-alkyl, C$_1$-C$_4$-alkoxy, halo, nitro, amino, C$_1$-C$_4$-alkylthio, and mono- or di-C$_1$-C$_4$-alkylamino, or NR$_4$R$_5$, where R$_4$ R$_5$ are independently selected from hydrogen, C$_1$-C$_6$-straight- or branched-alkyl, unsubstituted or mono-, di-, or trisubstituted-carboxy-$C_1$-$C_8$-straight- or branched-alkyl, or unsubstituted or mono-, di-, or trisubstituted-carboxamido-$C_1$-$C_8$-straight- or branched-alkyl, wherein the substituent(s) on the carboxy-$C_1$-$C_8$-straight- or branched-alkyl or on the carboxamido-$C_1$-$C_8$-straight- or branched-alkyl is/are selected from the group consisting of $C_1$-$C_4$-alkyl, $C_1$-$C_4$-alkoxy, amino-$C_1$-$C_4$-alkyl, unsubstituted or mono-, di-, or trisubstituted $C_6$- or $C_{10}$-aryl, unsubstituted or mono-, di- or trisubstituted $C_6$- or $C_{10}$-aryl-$C_1$-$C_8$-alkyl, and unsubstituted or mono-, di-, or trisubstituted $C_6$- or $C_{10}$-aryl-$C_1$-$C_4$-alkoxy, where the substituent(s) on the $C_6$- or $C_{10}$-aryl, the $C_6$- or $C_{10}$-aryl-$C_1$-$C_8$-alkyl or the $C_6$- or $C_{10}$-aryl-$C_1$-$C_4$-alkoxy is/are selected from the group consisting of hydroxy, $C_1$-$C_8$straight- or branched-alkyl, $C_1$-$C_4$-alkoxy, halo, nitro, amino, $C_1$-$C_4$-alkylthio, and mono- or di-$C_1$-$C_4$-alkylamino;

$R^1$ is $R^a$ or $R^b$;

$R^a$ is unsubstituted or mono-, di- or trisubstituted aryl, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino; unsubstituted or mono-, di- or trisubstituted heteroaryl, and the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino; unsubstituted or mono-, di- or trisubstituted $C_6$- or $C_{10}$-aryl-$C_1$-$C_8$-straight- or branched-alkyl, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino; unsubstituted or mono-, di- or trisubstituted heteroaryl-$C_1$-$C_8$-straight- or branched-alkyl, and the substituent(s) is/are selected from the group consisting of $C_1$-$C_8$-straight- or branched alkyl, hydroxy, $C_1$-$C_4$-alkoxy, halo, nitro, amino, $C_1$-$C_4$-alkylthio and mono- or di-$C_1$-$C_4$-alkylamino; unsubstituted or mono-, di- or trisubstituted $C_6$-or $C_{10}$-aryl-$C_2$-$C_4$-alkenyl, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$ alkylamino; unsubstituted or mono-, di- or trisubstituted heteroaryl-$C_2$-$C_4$-alkenyl, and the sub-stituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino; unsubstituted or mono-, di- or trisubstituted $C_6$- or $C_{10}$-aryloxy, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkyl-thio and mono- or di-$C_1$-$C_4$-alkylamino; unsubstituted or mono-, di- or trisubstituted heteroaryloxy, and the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino; unsubstituted or mono-, di- or trisubstituted $C_6$- or $C_{10}$-arylthio, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkyl-thio or mono- or di-$C_1$-$C_4$-alkylamino; unsubstituted or mono-, di- or trisubstituted heteroarylthio, and the substituent(s) is/are selected from the group consisting of $C_1$-$C_8$-straight- or branched alkyl, hydroxy, $C_1$-$C_4$-alkoxy, halo, nitro, amino, $C_1$-$C_4$-alkylthio or mono- or di-$C_1$-$C_4$-alkylamino; unsubstituted or mono-, di- or trisubstituted $C_6$- or $C_{10}$-aryl-$C_1$-$C_4$-alkyloxy, where the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio or mono- or di-$C_1$-$C_4$-alkylamino; unsubstituted or mono-, di- or trisubstituted heteroaryl-$C_1$-$C_4$-alkyloxy, and the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio or mono- or di-$C_1$-$C_4$-alkylamino; unsubstituted or mono-, di- or trisubstituted mono- or $C_{10}$-aryl-$C_1$-$C_4$-alkylthio, where substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino; unsubstituted or mono-, di- or trisubstituted heteroaryl-$C_1$-$C_4$-alkylthio, and the substituent(s) is/are selected from the group consisting of $C_1$-$C_8$-straight- or branched-alkyl, hydroxy, $C_1$-$C_4$-alkoxy, halo, nitro, amino, $C_1$-$C_4$-alkylthio and mono- or di-$C_1$-$C_4$-alkylamino; $C_1$-$C_8$-straight- or branched-alkyls; $C_3$-$C_{10}$-cycloalkyl; $C_3$-$C_{10}$-cycloalkyl-$C_1$-$C_4$-alkyl; $C_1$-$C_6$-straight- or branched-alkyl-Q-$(CH_2)_m$, here m is 1-to-3, and Q is O, S, SO, $SO_2$, —HC=CH—, or substituted-amino, wherein the substituent is hydrogen, $C_1$-$C_8$-straight- or branched-alkyl, unsubstituted or mono-, di- or trisubstituted $C_6$- or $C_{10}$-aryl, unsubstituted or mono-, di or trisubstituted heteroaryl, unsubstituted or mono-, di- or trisubstituted $C_6$- or $C_{10}$-aryl-$C_1$-$C_4$-alkyl, or unsubstituted or mono-, di- or trisubstituted heteroaryl where the substituent(s) on the $C_6$- or $C_{10}$-aryl, the heteroaryl, the $C_6$- or $C_{10}$-aryl-$C_1$-$C_4$-alkyl, or the heteroaryl $C_1$-$C_4$-alkyl is/are selected from the group consisting of $C_1$-$C_8$-straight- or branched-alkyl, hydroxy, $C_1$-$C_4$alkoxy, halo, nitro, amino, $C_1$-$C_4$-alkyl-thio and mono- or di-$C_1$-$C_4$-alkylamino; or $C_9$-$C_{12}$-benzofused cycloalkyls; and $R^b$ is —$CHR^2R^3$, where $R^2$ is $R^a$, as defined above, and $R^3$ is substituted carbonyl, wherein the substituent is hydroxy, $C_1$-$C_4$-alkoxy, $C_1$-$C_4$-alkyl, hydroxy-$C_1$-$C_4$-alkyl, amino, $C_1$-$C_8$-straight- or branched-alkylamino, $C_6$- or $C_{10}$-aryloxy, $C_6$- or $C_{10}$-aryl-$C_1$-$C_6$-alkylamino, $C_6$- or $C_{10}$-aryl-$C_1$-$C_4$-alkyloxy, carboxy-$C_1$-$C_8$-straight- or branched-alkylamino, or carboxamido-$C_1$-$C_8$-straight- or branched-alkylamino; $NR^7R^8$ wherein $R^7$ and $R^8$ are independently selected from hydrogen, substituted carbonyl, unsubstituted or mono-, di- or trisubstituted-carboxy-$C_1$-$C_8$-straight- or branched-alkyl, and unsubstituted- or mono-, di- or trisubstituted-carboxamido-$C_1$-$C_8$-straight- or branched-alkyl, where the substituents on the carbonyl, the carboxy-$C_1$-$C_8$-alkyl or the carboxamido-$C_1$-$C_8$-alkyl is/are selected from $C_1$-$C_4$-alkyl, $C_1$-$C_4$-alkyloxy, amino-$C_1$-$C_4$-alkyl, unsubstituted or mono-, di- or trisubstituted $C_6$- or $C_{10}$-aryl-$C_1$–$C_8$-alkyl, unsubstituted- or mono-, di- or trisubstituted $C_6$- or $C_{10}$-aryl, unsubstituted- or mono-, di- or trisubstituted $C_6$- or $C_{10}$-aryl-$C_1$–$C_4$-alkoxy, and mono-, di- or trisubstituted-$C_1$–$C_8$-alkyl, wherein the substituent(s) on the $C_6$- or $C_{10}$-aryl-$C_1$–$C_8$-alkyl, the $C_6$- or $C_{10}$-aryl, the $C_6$- or $C_{10}$-aryl-$C_1$–$C_4$-alkoxy or the $C_1$–$C_8$-alkyl is/are selected from hydroxy, $C_1$–$C_8$-straight- or branched-alkyl, $C_1$–$C_4$-alkoxy, halo, nitro, amino, $C_1$–$C_4$-alkylthio, or mono- or di-$C_1$–$C_4$-alkylamino;

$R^6$ is hydrogen; halo; hydroxy; nitro; amino; $C_1$–$C_4$-alkylamino; $C_1$–$C_8$-alkyl; or $C_1$–$C_8$alkoxy;

y is 1 to 3;

p is 0 to 2, with the proviso that when p is 0, X is carbonyl;

wherein heteroaryl represents a group selected from the group consisting of pyridyl, thienyl, furyl, imidazoyl, thiazolyl, indolyl, quinolinyl, isoquinolinyl, benzimidazolyl, benzothiazolyl, and benzthienyl; and the pharmaceutically-acceptable salts thereof.

2. A compound according to claim 1 which is a member of the group:

1-carbomethoxymethyl-3-(3-indolemethyl-)aminohomodihydrocarbostyril;
1-carboxymethyl-3-(carbonyl-2-indolyl-)aminohomodihydrocarbostyril;
1-t-butoxycarbonylmethyl-3-(2-naphthylacetyl-)aminohomodihydrocarbostyril;
1-t-butoxycarbonylmethyl-3-(D-N-acetyltryptophanyl-)aminohomodihydrocarbostyril;
1-t-butoxycarbonylmethyl-3-(L-N-acetyltryptophanyl-)aminohomodihydrocarbostyril;
1-t-butoxycarbonylmethyl-3-(L-N-carbobenzyloxytryptophanyl)aminohomodihydrocarbostyril;
1-t-butoxycarbonylmethyl-3-(D-N-carbobenzyloxytryptophanyl)aminohomodihydrocarbostyril;
1-t-butoxycarbonylmethyl-3-(carbonyl-2-indolyl-)aminohexahydrobenzoazocine-2-one;
1-t-butoxycarbonylmethyl-3-(2-naphthoyl-)aminohomodihydrocarbostyril;
1-t-butoxycarbonylmethyl-3-(2-naphthylmethyl-)aminohomodihydrocarbostyril;
1-t-butoxycarbonylmethyl-3-(carbonyl-2-indolyl-)aminohomodihydrocarbostyril;
1-t-butoxycarbonylmethyl-3-(2-naphthylmethyl-)aminohomodihydrocarbostyril;
1-t-butoxycarbonylmethyl-3-(3,4-dichlorobenzoyl-)aminohomodihydrocarbostyril;
1-t-butoxycarbonylmethyl-3-(2-indolemethyl-)aminohomodihydrocarbostyril;
1-t-butoxycarbonylmethyl-3-(3,4-dichlorobenzyl-)aminohomodihydrocarbostyril;
1-benzyl-3-(carbonyl-2-indolyl)aminohomodihydrocarbostyril;
1-ethoxycarbonylmethyl-3-(2-naphthoyl-)aminohomodihydrocarbostyril;
1-butoxycarbonylmethyl-3(R)-(2-indolemethyl-)aminohomodihydrocarbostyril;
1-t-butoxycarbonylmethyl-3(R)-3,4-dichlorobenzyl-)aminohomodihydrocarbostyril;
1-t-butoxycarbonylmethyl-3(R)-(2-naphthylmethyl)-aminohomodihydrocarbostyril;
1-t-butoxycarbonylmethyl-3(R)-(2-naphthoyl-)aminohomodihydrocarbostyril; and
1-t-butoxycarbonylmethyl-3(R)-(carbonyl-2-indolyl-)aminohomodihydrocarbostyril.

3. A compound according to claim 2 which is a member of the group:

1-t-carboxymethyl-3-(carbonyl-2-indolyl-)aminohomodihydrocarbostyril;
1-benzyl-3-(carbonyl-2-indolyl)aminohomodihydrocarbostyril;
1-t-butoxycarbonylmethyl-3-(carbonyl-2-indolyl-)aminohomodihydrocarbostyril;
1-t-butoxycarbonylmethyl-3-(2-indolemethyl-)aminohomodihydrocarbostyril;
1-t-butoxycarbonylmethyl-3-(3,4-dichlorobenzyl-)aminohomodihydrocarbostyril;
1-t-butoxycarbonylmethyl-3(R)-(2-indolemethyl-)aminohomodihydrocarbostyril;
1-t-butoxycarbonylmethyl-3(R)-(3,4-dichlorobenzyl-)aminohomodihydrocarbostyril;
1-t-butoxycarbonylmethyl-3(R)-(2-naphthylmethyl-)aminohomodihydrocarbostyril;
1-t-butoxycarbonylmethyl-3(R)-(2-naphthoyl-)aminohomodihydrocarbostyril; and
1-t-butoxycarbonylmethyl-3(R)-(carbonyl-2-indolyl-)aminohomodihydrocarbostyril.

* * * * *